United States Patent
Isono et al.

(10) Patent No.: US 8,187,787 B2
(45) Date of Patent: *May 29, 2012

(54) FLUORINE-CONTAINING COMPOUND, FLUORINE-CONTAINING POLYMER, NEGATIVE-TYPE RESIST COMPOSITION, AND PATTERNING PROCESS USING SAME

(75) Inventors: Yoshimi Isono, Kawagoe (JP); Jonathan Joachim Jodry, Kawagoe (JP); Satoru Narizuka, Saitama (JP); Kazuhiro Yamanaka, Kokubunji (JP)

(73) Assignee: Central Glass Company, Limited, Ube-shi (JP)

( * ) Notice: Subject to any disclaimer, the term of this patent is extended or adjusted under 35 U.S.C. 154(b) by 54 days.

This patent is subject to a terminal disclaimer.

(21) Appl. No.: 12/146,889

(22) Filed: Jun. 26, 2008

(65) Prior Publication Data

US 2009/0011199 A1 Jan. 8, 2009

(30) Foreign Application Priority Data

Jun. 29, 2007 (JP) ................................ 2007-171742

(51) Int. Cl.
*G03C 1/00* (2006.01)
*C08F 16/24* (2006.01)

(52) U.S. Cl. ...................... 430/270.1; 430/326; 430/907; 430/914; 430/942; 430/966; 526/242; 526/245; 526/247

(58) Field of Classification Search .................. 526/245, 526/247, 242, 281, 283, 318, 318.1, 318.2, 526/318.3, 334; 562/472, 495, 595, 598, 562/605

See application file for complete search history.

(56) References Cited

U.S. PATENT DOCUMENTS

| | | | | |
|---|---|---|---|---|
| 4,150,067 | A * | 4/1979 | Dawans et al. | 526/171 |
| 5,126,482 | A * | 6/1992 | Nakai et al. | 554/150 |
| 7,186,773 | B2 * | 3/2007 | Araki et al. | 524/553 |
| 7,217,496 | B2 * | 5/2007 | Khojasteh et al. | 430/270.1 |
| 7,906,269 | B2 * | 3/2011 | Isono et al. | 430/270.1 |
| 2004/0192867 | A1 * | 9/2004 | Narita et al. | 526/242 |
| 2004/0214103 | A1 | 10/2004 | Araki et al. | |
| 2005/0131145 | A1 * | 6/2005 | Morita et al. | 525/173 |
| 2006/0004129 | A1 * | 1/2006 | Otozawa et al. | 524/284 |
| 2006/0105269 | A1 | 5/2006 | Khojasteh et al. | |
| 2006/0264592 | A1 * | 11/2006 | Kobayashi et al. | 526/246 |

FOREIGN PATENT DOCUMENTS

| | | |
|---|---|---|
| EP | 0 232 972 A2 | 8/1987 |
| JP | 1-242551 A | 9/1989 |
| JP | 8-3635 B2 | 1/1996 |

OTHER PUBLICATIONS

Billmeyer, Jr. Textbook of Polymer Science, 1984, John Wiley & Sons, 3rd edition, p. 18.*
Shigeyuki Iwasa et al., "Novel negative photoresist based on polar alicyclic polymers for ArF excimer laser lithography", SPIE, Advances in Resist Technology and Processing XIV, vol. 3333, pp. 417-424, (1998).
E. Ann Hallinan et al., "2,2-Difluoro-3-Hydroxyesters by Reformatskii Reaction", Tetrahedron Letters, vol. 25, No. 22, pp. 2301-2302, (1984).
Taiwanese Office Action with English translation dated Mar. 2, 2012 (fifteen (15) pages).
Taiwanese Search Report with English translation dated Feb. 29, 2012 (two (2) pages).

* cited by examiner

*Primary Examiner* — Peter F Godenschwager
*Assistant Examiner* — Nicole M Buie-Hatcher
(74) *Attorney, Agent, or Firm* — Crowell & Moring LLP

(57) ABSTRACT

Disclosed is a fluorine-containing unsaturated carboxylic acid represented by formula (1),

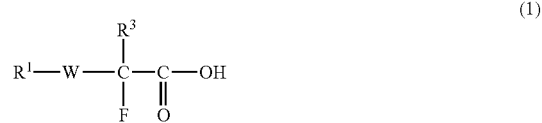

(1)

wherein $R^1$ represents a polymerizable double-bond containing group, $R^3$ represents a fluorine atom or fluorine-containing alkyl group, and W represents a bivalent linking group. This compound can provide a fluorine-containing polymer compound that has a weight-average molecular weight of 1,000-1,000,000 and contains a repeating unit represented by formula (2),

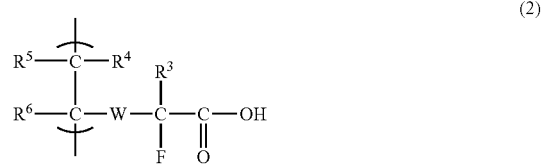

(2)

wherein $R^3$ and W are defined as above, each of $R^4$, $R^5$ and $R^6$ independently represents a hydrogen atom, fluorine atom or monovalent organic group, at least two of $R^4$, $R^5$ and $R^6$ may be combined to form a ring. This polymer compound can provide a chemically amplified resist composition that is transparent to KrF or ArF excimer laser light and has a high resolution and is capable of forming a pattern having a rectangular section with no swelling.

16 Claims, No Drawings

FLUORINE-CONTAINING COMPOUND, FLUORINE-CONTAINING POLYMER, NEGATIVE-TYPE RESIST COMPOSITION, AND PATTERNING PROCESS USING SAME

BACKGROUND OF THE INVENTION

The present invention relates to a fluorine-containing unsaturated carboxylic acid, a fluorine-containing polymer compound obtained by polymerization of the carboxylic acid, a negative-type resist composition containing the polymer compound, and a pattern forming process by using the resist composition.

Various devices such as semiconductor devices are required to have higher density and higher integration. In particular, a demand for a photolithography that makes microfabrication possible has become strict year to year. For producing a DRAM having an integration degree of 1G bits or more, it is necessary to have a processing technology of a minimum line width of 0.13 micrometers or less. In response to this, a photolithography using KrF excimer laser (248 nm) or ArF excimer laser (193 nm) is used. Furthermore, the development of a photolithography using $F_2$ excimer laser (157 nm) is in progress for the purpose of forming finer patterns.

Hitherto, as a negative-type resist material used in the circuit pattern formation by i-ray or KrF excimer laser light (248 nm) as a light source, there has been a chemically amplified, negative-type resist composition containing a combination of acid generator, a resin (e.g., novolac resin and polyhydroxystyrene) soluble in alkali aqueous solution, and an amino resin (e.g., melamine resin and urea resin) (see Japanese Patent Examined Publication 8-3635 B and its corresponding European Patent Application Publication 0232972 A2).

As a negative-type resist composition used in exposure to ArF excimer laser having a shorter wavelength, there is a negative-type resist composition (see SPIE Advances in Resist Technology and Processing XIV, Vol. 3333, p. 417-424 (1998)) that contains a carboxyl-containing resin component improved in transparency to ArF excimer laser, a crosslinking agent having an alcoholic hydroxy group, and an acid generator. In this composition, the carboxyl group contained in the resin component reacts with the alcoholic hydroxy group of the crosslinking agent by an action of the acid from the acid generator, thereby changing the resin component from alkali-soluble to alkali-insoluble. In a negative-type resist of such composition, it is possible to form a negative-type pattern upon exposure as a result of the formation of an ester bond between the crosslinking agent and the resin component in the presence of acid. In the negative-type resist composition, it has been possible to adjust solubility by introducing a carboxyl group as a moiety for providing solubility function, but it has not been possible to decrease swelling at the same time.

As carboxylic acid compounds having a fluorine atom at α-position, 2-fluoro-phenylacetic acid and its esters (see Japanese Patent Application Publication 1-242551) and ethyl 2,2-difluoro-3-hydroxy-3-phenylpropionate (see Tetrahedron Letters, Vo. 25, No. 22, pp 2301-2302, 1984) are known.

SUMMARY OF THE INVENTION

The present inventors have examined a phenomenon in which a negative-type resist that has been made to be alkali-insoluble through crosslinking by exposure swells by development with an alkali aqueous solution. Thus, we have obtained new findings, as follows. It is possible to decrease the concentration of acid group in the resist film by increasing acid strength of the acid group for providing alkali solubility. In case that the acid group is an ordinary carboxylic acid or the like, however, this acid strength increase also increases the capacity to generate swelling. As a result, the tendency of having swelling does not change. In view of such findings, we have tried to increase acidity by modifying a chemical structure near the carboxyl group and have succeeded in decreasing the degree of swelling by alkali aqueous solution, while increasing solubility in alkali aqueous solution with a relatively low density carboxylic group, thereby completing the present invention.

In fact, a negative-type resist composition of the present invention, which contains an alkali-soluble resin component, an acid generator for generating acid by exposure and a crosslinking agent, has a fluorine atom at α-position of carboxylic group. With this, it is possible to increase acidity of the carboxylic group. Furthermore, chemical stability of a structure near the carboxylic group in alkali aqueous solution is maintained in the resist composition. Therefore, it is possible to maintain alkali solubility even if the concentration of carboxylic group in the resist film is lowered. Furthermore, it is possible to prevent swelling of the resist film.

According to the present invention, there is provided a fluorine-containing unsaturated carboxylic acid represented by formula (1),

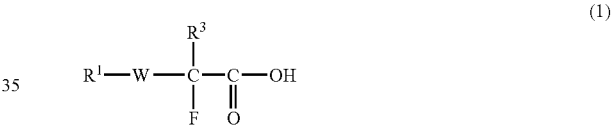

(1)

wherein $R^1$ represents a polymerizable double-bond containing group, $R^3$ represents a fluorine atom or fluorine-containing alkyl group, and W represents a bivalent linking group.

According to the present invention, there is provided a fluorine-containing polymer compound comprising a repeating unit (a) represented by formula (2),

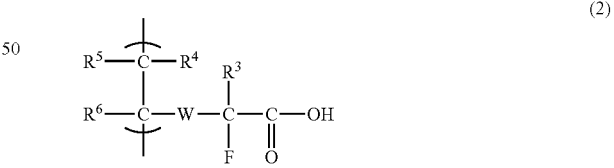

(2)

wherein $R^3$ and W are defined as in formula (1), each of $R^4$, $R^5$ and $R^6$ independently represents a hydrogen atom, fluorine atom or monovalent organic group, and at least two of $R^4$, $R^5$ and $R^6$ may be combined to form a ring, wherein the fluorine-containing polymer compound has a weight-average molecular weight of 1,000 to 1,000,000.

A partial structure $R^1$—W— in formula (1) may include a group selected from the group consisting of the following seven groups,

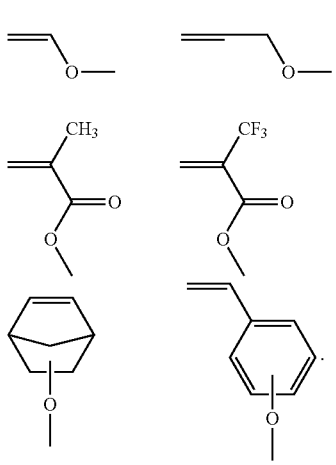

A partial structure, which is contained in formula (2) and is represented by formula (19-1),

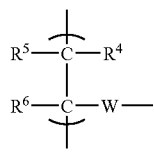

(19-1)

may have a structure obtained by cleavage of a polymerizable double-bond of a group selected from the group consisting of the above seven groups.

In formula (1) or (2), W may represent a bivalent linking group selected from the group consisting of a single bond, —$(CR^7R^8)_n$— (wherein n represents an integer of 1-10, each of $R^7$ and $R^8$ independently represents a monovalent organic group, and $R^7$ and $R^8$ may be combined to form a ring), —O—, —C(=O)—, —C(=O)O—, —O—C(=O)—, a bivalent alicyclic hydrocarbon group, a bivalent aromatic hydrocarbon group, a thioether group, an ester group, an amide group, a sulfonamide group, a urethane group, a urea group, and combinations of these.

The fluorine-containing unsaturated carboxylic acid may be selected from the group consisting of the following seven compounds,

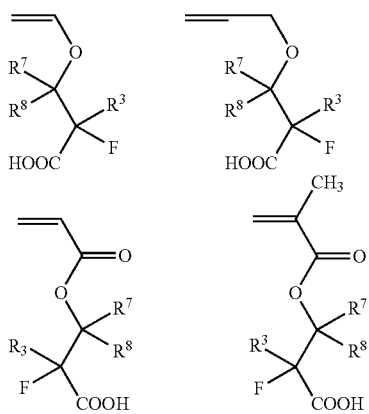

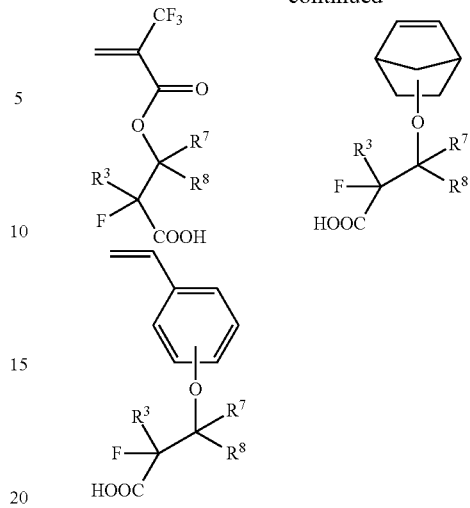

wherein $R^3$ represents a fluorine atom or trifluoromethyl group, $R^7$ represents a hydrogen atom or a straight-chain, branched or cyclic alkyl or fluoroalkyl group, $R^8$ represents a straight-chain, branched or cyclic alkyl or fluoroalkyl group, and $R^7$ and $R^8$ may be combined to form a ring.

The fluorine-containing polymer compound may have a structure obtained by cleavage of a polymerizable double-bond of a compound selected from the group consisting of the same seven compounds as above. In the above seven compounds, each of $R^7$ and $R^8$ independently may represent a $C_1$-$C_4$ straight-chain or branched alkyl or fluoroalkyl group or a $C_3$-$C_{10}$ cyclic alkyl or fluoroalkyl group, or $R^7$ and $R^8$ are bonded together to form a $C_4$-$C_8$ alicyclic hydrocarbon group.

In the above seven compounds, $R^7$ may represent a hydrogen atom or a monovalent organic group selected from the group consisting of methyl group, ethyl group, propyl group, butyl group, cyclopentyl group, cyclohexyl group, norbornyl group, adamantyl group, trifluoromethyl group, 2,2,2-trifluoroethyl group, 1-(trifluoromethyl)ethyl group, and 3,3,3-trifluoropropyl group, and $R^8$ may represent a monovalent organic group selected from the group consisting of methyl group, ethyl group, propyl group, butyl group, cyclopentyl group, cyclohexyl group, norbornyl group, adamantyl group, trifluoromethyl group, 2,2,2-trifluoroethyl group, 1-(trifluoromethyl)ethyl group, and 3,3,3-trifluoropropyl group. Alternatively, $R^7$ and $R^8$ may be bonded together to form a cyclopentyl group, cyclohexyl group or cycloheptyl group.

The fluorine-containing unsaturated carboxylic acid may be represented by one of the following two formulas,

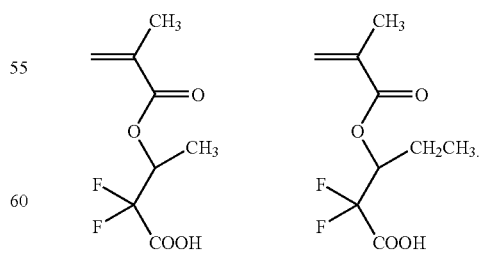

The fluorine-containing polymer compound may have a structure obtained by cleavage of a polymerizable double-bond of a fluorine-containing unsaturated carboxylic acid represented by one of the above two formulas.

The fluorine-containing polymer compound may further include a repeating unit (b) having an alcoholic hydroxy group.

The repeating unit (b) may be a repeating unit represented by formula (7),

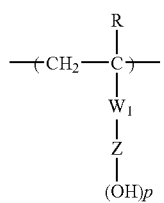

(7)

wherein R represents a hydrogen atom, alkyl group, halogenated alkyl group, halogen atom, or hydroxyalkyl group;

$W_1$ represents a single bond, —C(=O)—O—, or —O—;

Z represents an alicyclic hydrocarbon group, an aliphatic acyclic hydrocarbon group, or an organic group formed of a combination of these groups, each of these groups having a valence of "p+1";

p represents an integer of 0-3; and

R represents a hydroxyalkyl group when p=0.

The repeating unit (b) may be a repeating unit represented by formula (7-1),

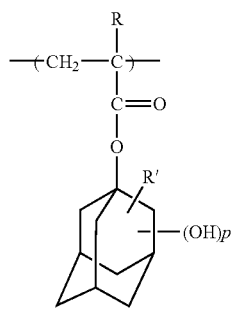

(7-1)

wherein R represents a hydrogen atom, alkyl group, halogen atom, or halogenated alkyl group;

R' represents a hydrogen atom, alkyl group, or $C_1$-$C_5$ alkoxy group; and p represents an integer of 1-3.

The fluorine-containing polymer may further include a repeating unit (c) having a side chain with a lactone ring.

The fluorine-containing polymer compound may further include at least one repeating unit formed by cleavage of at least one polymerizable double bond of at least one compound selected from the group consisting of acrylates, fluorine-containing acrylates, methacrylates, fluorine-containing methacrylates, styrene compounds, fluorine-containing styrene compounds, vinyl ethers, fluorine-containing vinyl ethers, allyl ethers, fluorine-containing allyl ethers, acrylamides, methacrylamides, vinyl esters, allyl esters, olefins, fluorine-containing olefins, norbornene compounds, fluorine-containing norbornene compounds, sulfur dioxide, and vinyl silanes.

In the fluorine-containing polymer compound, the repeating unit (a) may be in 1-99 mol %, based on a total mole number of all repeating units contained in the fluorine-containing polymer compound.

In the fluorine-containing polymer compound, the repeating unit (a) and the repeating unit (b) may respectively be in 1-99 mol % and 1-90 mol %, based on a total mole number of all repeating units contained in the fluorine-containing polymer compound.

The fluorine-containing polymer compound may include a repeating unit (d), and the repeating units (a) to (d) may respectively be in 1-99 mol %, 1-90 mol %, 10-90 mol % and 0-70 mol %, based on a total mole number of all repeating units contained in the fluorine-containing polymer compound.

According to the present invention, there is provided a negative-type resist composition including the fluorine-containing polymer compound as an alkali-soluble resin component; an acid generator for generating an acid by exposure; and a crosslinking agent.

According to the present invention, there is provided a process for forming a resist pattern, including the steps of:

(a) applying the resist composition on a substrate to form a resist film;

(b) exposing the resist film; and (c) developing the exposed resist film.

The step (b) may be conducted by exposing the resist film to a high energy ray that is a near-ultraviolet ray, vacuum ultraviolet ray, extreme ultraviolet ray, or soft X-ray.

According to the present invention, there is provided an electronic device including a circuit pattern formed by the process.

DETAILED DESCRIPTION

In the specification and the claims, alkyl group is defined as containing a straight-chain, branched or cyclic alkyl group. Cyclic alkyl group is defined as a part of alicyclic group or alicyclic hydrocarbon group. The term of "lower" as in lower alkyl group and other groups refers to a carbon atom number of 1-4. However, the term of "lower" as to cyclic alkyl group refers to one having a cyclic structure of a carbon atom number of 3-10, and cyclic alkyl group may have a lower alkyl group (e.g., methyl group, ethyl group, propyl group, butyl group, cyclopentyl group, cyclohexyl group, norbornyl group, adamantyl group, trifluoromethyl group, 2,2,2-trifluoroethyl group, 1-(trifluoromethyl)ethyl group, and 3,3,3-trifluoropropyl group) as a substituent. Hereinafter, when a compound having isomers is exemplified, only its typical name and structure may be described for simplification, but it is defined as including all of its isomers.

In the specification, halogen refers to fluorine, chlorine, bromine or iodine.

It is possible to form a resist pattern superior in rectangularity and resolution, by the resist pattern forming process using the negative-type resist composition containing the fluorine-containing polymer compound having the repeating unit (a) derived from the fluorine-containing unsaturated carboxylic acid. The fluorine-containing unsaturated carboxylic acid is suitable for introducing a carboxylic acid that is high in acidity into its polymer compound.

In the following, the present invention is exemplarily described in detail by embodiments. The present invention is, however, not limited to the embodiments. A skilled person in the art may suitably conduct a modification, improvement or the like on the following embodiments without deviating from the gist of the present invention, and such modification, improvement or the like is in the scope of the present invention.

As stated above, a negative-type resist composition of the present invention contains an alkali-soluble resin component (Component (A)), an acid generator (Component (B)) for generating acid by exposure, and a crosslinking agent (Component (C)).

Negative-type resist composition is soluble in alkali solution prior to exposure. By exposure, acid is generated from the acid generator. By an action of this acid, a crosslinking occurs between the alkali-soluble resin component and the crosslinking agent, thereby making it insoluble in alkali solution. In a resist pattern formation, when a resist film formed on substrate is position-selectively exposed, the exposed portion becomes insoluble in alkali solution, and in contrast the unexposed portion is still alkali-soluble. Therefore, it is possible to form a negative-type resist pattern by developing the resist film with alkali solution.

COMPONENT (A)

Alkali-Soluble Resin Component

The alkali-soluble resin component in the negative-type resist composition may be a fluorine-containing polymer compound containing at least a repeating unit (a) that is represented by formula (2) and is formed by cleavage of a polymerizable double bond of the fluorine-containing unsaturated carboxylic acid represented by formula (1), and a repeating unit (b) having an alcoholic hydroxy group at its side chain As shown in formula (2), the fluorine-containing polymer compound is characterized in that a chain skeleton formed through cleavage of the polymerizable double bond is bonded to a carboxyl group (COOH) through a bivalent linking group W and that this carboxyl group is bonded to the bivalent linking group W through α-position carbon, to which a fluorine atom and a fluorine atom or fluorine-containing alkyl group $R^3$ are bonded.

Repeating Unit (a)

As stated above, $R^3$, which is bonded to α-position carbon attached to carboxyl group in the fluorine-containing unsaturated carboxylic acid represented by formulas (1) and in the repeating unit (a) represented by formula (2), is a fluorine atom or fluorine-containing alkyl group. Although this fluorine-containing alkyl group is not particularly limited, it may have a carbon atom number of 1-12, preferably 1-3. Its examples include trifluoromethyl group, pentafluoroethyl group, 2,2,2-trifluoroethyl group, n-heptafluoropropyl group, 2,2,3,3,3-pentafluoropropyl group, 3,3,3-trifluoropropyl group, and hexafluoroisopropyl group. $R^3$ is more preferably a fluorine atom or trifluoromethyl group.

The bivalent linking group W in formula (1) or (2) may be selected from a single bond, —$(CR^7R^8)_n$— (wherein n represents an integer of 1-10, each of $R^7$ and $R^8$ independently represents a monovalent organic group, and $R^7$ and $R^8$ may be combined to form a ring), —O—, —C(=O)—, —C(=O)O—, —O—C(=O)—, a bivalent alicyclic hydrocarbon group, a bivalent aromatic hydrocarbon group, a thioether group, an ester group, an amide group, a sulfonamide group, urethane group, a urea group, and combinations of these.

The bivalent alicyclic hydrocarbon group may be a group obtained by removing two hydrogen atoms from an alicyclic compound (e.g., norbornane and adamantane). The bivalent aromatic hydrocarbon group may be a group obtained by removing two hydrogen atoms from an aromatic compound (e.g., benzene).

The linking group W as a combination of the above-mentioned groups may be —$(CR^7R^8)_m$—C(=O)—O—$(CR^7R^8)_n$— or —$(CR^7R^8)_m$—$(CR^7R^8)_n$—, where each of m and n independently represents an integer of 0-10, m is preferably 0, n is preferably 1, and, when each of $R^7$ and $R^8$ is contained in a plural number, they may be the same or different.

The monovalent organic group $R^7$ or $R^8$ of the substituted methylene group —$CR^7R^8$— is not particularly limited. It may be a hydrogen atom, hydroxy group, or a $C_1$-$C_{30}$ monovalent organic group selected from alkyl groups, alicyclic hydrocarbon groups, substituted alkyl groups, alkoxy groups, aryl groups, and condensed polycyclic aromatic groups. These monovalent organic groups can have fluorine atom, oxygen atom, sulfur atom, nitrogen atom, and/or carbon-carbon double bond. The groups $R^7$ and $R^8$ may be the same or different between $R^7$'s, between $R^8$'s, and between $R^7$ and $R^8$. $R^7$ and $R^8$ may be combined to form a ring. This ring is preferably an alicyclic hydrocarbon group.

The alkyl group as $R^7$ or $R^8$ may be one having a carbon number of 1-30, preferably 1-12. For example, it is possible to cite methyl group, ethyl group, n-propyl group, i-propyl group, n-butyl group, 1-methylpropyl group, 2-methylpropyl group, tert-butyl group, n-pentyl group, i-pentyl group, 1,1-dimethylpropyl group, 1-methylbutyl group, 1,1-dimethylbutyl group, n-hexyl group, n-heptyl group, i-hexyl group, n-octyl group, i-octyl group, 2-ethylhexyl group, n-nonyl group, n-decyl group, n-undecyl group, and n-dodecyl group. Of these, lower alkyl groups are preferable. Particularly preferable ones are methyl group, ethyl group, n-propyl group, and i-propyl group.

Examples of the substituted alkyl group as $R^7$ or $R^8$ include ones in which at least one of hydrogen atoms of the alkyl group has been replaced with a $C_1$-$C_4$ alkoxy group, halogen atom, acyl group, acyloxy group, cyano group, hydroxyl group, carboxyl group, alkoxycarbonyl group, nitro group, or the like. A fluoroalkyl group in which at least one of hydrogen atoms of the alkyl group has been replaced with a fluorine atom(s) is preferable. Specific examples of the substituted alkyl group include lower fluoroalkyl groups such as trifluoromethyl group, pentafluoroethyl group, 2,2,2-trifluoroethyl group, n-heptafluoropropyl group, 2,2,3,3,3-pentafluoropropyl group, 3,3,3-trifluoropropyl group, and hexafluoroisopropyl group.

The alkoxy group as $R^7$ or $R^8$ may be a $C_1$-$C_4$ alkoxy group, such as methoxy group, ethoxy group, propoxy group, and butoxy group.

The aryl group as $R^7$ or $R^8$ may be a $C_1$-$C_{30}$ aryl group. As a monocyclic aryl group, it is preferable to use one having a ring carbon number of 3-12, more preferably 3-6. Examples include phenyl group, biphenyl group, terphenyl group, o-tolyl group, m-tolyl group, p-tolyl group, p-hydroxyphenyl group, p-methoxyphenyl group, mesityl group, o-cumenyl group, 2,3-xylyl group, 2,4-xylyl group, 2,5-xylyl group, 2,6-xylyl group, 3,4-xylyl group, 3,5-xylyl group, o-fluorophenyl group, m-fluorophenyl group, p-fluorophenyl group, o-trifluoromethylphenyl group, m-trifluoromethylphenyl group, p-trifluoromethylphenyl group, 2,3-bis(trifluoromethyl)phenyl group, 2,4-bis(trifluoromethyl)phenyl group, 2,5-bis(trifluoromethyl)phenyl group, 2,6-bis(trifluoromethyl)phenyl group, 3,4-bis(trifluoromethyl)phenyl group, 3,5-bis(trifluoromethyl)phenyl group, p-chlorophenyl group, p-bromophenyl group, and p-iodophenyl group.

The $C_1$-$C_{30}$ condensed polycyclic aromatic group as $R^7$ or $R^8$ may be a monovalent organic group, such as pentalenyl group, indenyl group, naphthyl group, azlenyl group, heptalenyl group, biphenylenyl group, indacenyl group, acenaphthylenyl group, fluorenyl group, phenarenyl group, phenanthryl group, anthryl group, fluoranthenyl group, acephenanthrylenyl group, aceanthrylenyl group, triphenylenyl group, pyrenyl group, chrysenyl group, naphthacenyl group, picenyl group, perylenyl group, pentaphenyl group, pentacenyl group, tetraphenylenyl group, hexaphenyl group, hexacenyl group, rubicenyl group, coronenyl group, trinaphthylenyl group, heptaphenyl group, heptacenyl group, pyranthrenyl group, and ovalenyl group. It is possible to cite ones in which at least one hydrogen atom of these groups has been replaced with a fluorine atom(s) or a $C_1$-$C_4$ alkyl or fluorine-containing alkyl group, as preferable ones.

Examples of a monocyclic or polycyclic, heterocyclic group as $R^7$ or $R^8$ having a ring atom number of 3-25 include pyridyl group, furyl group, thienyl group, pyranyl group, pyrrolyl group, thiantrenyl group, pyrazolyl group, isothiazolyl group, isoxazolyl group, pyrazinyl group, pyrimidinyl group, pyridadinyl group, tetrahydropyranyl group, tetrahydrofuranyl group, tetrahydrothiopyranyl group, tetrahydrothiofuranyl group, 3-tetrahydrothiophen-1,1-dioxide group, and heterocyclic groups in which at least one hydrogen atom of the ring has been replaced with an alkyl group, alicyclic hydrocarbon group, aryl group or heterocyclic group. Of these, ones having a monocyclic or polycyclic ether ring or lactone ring are preferable, such as the following,

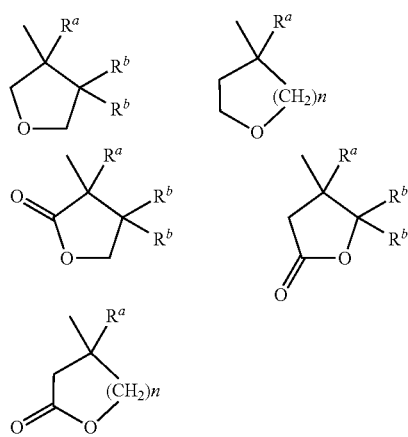

(3)

wherein each of $R^a$ and $R^b$ independently represents a hydrogen atom or $C_1$-$C_4$ alkyl group, and n represents an integer of 2-4.

As $R^7$ and $R^8$, a simple alicyclic hydrocarbon group or a combined alicyclic hydrocarbon group formed by simple alicyclic hydrocarbon groups that are combined together through carbon atoms may have a monocyclic or polycyclic structure. Specifically, these groups may have a monocyclo, bicyclo, tricyclo or tetracyclo structure of a carbon number of at least 3. The carbon number is preferably 3-30, more preferably 3-25. These alicyclic hydrocarbon groups may have substituents.

The alicyclic hydrocarbon group of monocyclic structure has a ring carbon number of preferably 3-12, more preferably 3-7. Its preferable examples include cyclopropyl group, cyclobutyl group, cyclopentyl group, cyclohexyl group, cycloheptyl group, cyclooctyl group, cyclodecanyl group, cyclododecanyl group, and 4-tert-butylcyclohexyl group. Examples of the alicyclic hydrocarbon group of polycyclic structure include those having a ring carbon number of 7-15, such as adamantyl group, noradamantyl group, decaline residue, tricyclodecanyl group, tetracyclododecanyl group, norbornyl group, and cedrol group.

The alicyclic hydrocarbon group may be a spiro ring, preferably having a carbon number of 3-6. Its preferable examples include adamantyl group, decaline residue, norbornyl group, cedrol group, cyclohexyl group, cycloheptyl group, cyclooctyl group, cyclodecanyl group, cyclododecanyl group, and tricyclodecanyl group. At least one hydrogen atom of the ring carbons or linking groups of these organic groups may independently be replaced with at least one $C_1$-$C_{25}$ alkyl or substituted alkyl group, hydroxy group, alkoxy group, carboxyl group, alkoxycarbonyl group, or a group in which at least one hydrogen atom of these groups has been replaced with at least one fluorine atom or trifluoromethyl group.

The alkyl group is preferably a lower alkyl group, more preferably an alkyl group selected from methyl group, ethyl group, propyl group, and isopropyl group. The substituted alkyl group may have a substituent that is a hydroxy group, halogen atom or alkoxy group. The alkoxy group may be a $C_1$-$C_4$ alkoxy group such as methoxy group, ethoxy group, propoxy group and butoxy group. The alkoxycarbonyl group may be a methoxycarbonyl group, ethoxycarbonyl group, or isopropoxycarbonyl group.

Specifically, the linking group W may be a single bond, —O—, —C(=O)—O—, —CH$_2$—O—, —O—CH$_2$—, —CH$_2$—C(=O)—O—, —C(=O)—O—CH$_2$, —CH$_2$—O—CH$_2$—, —CH$_2$—C(=O)—O—CH$_2$—, —C(=O)—O—CR$^7$R$^8$—, or —C$_6$H$_4$—O—CR$^7$R$^8$—. Herein, each of $R^7$ and $R^8$ is preferably and independently a hydrogen atom, fluorine atom, alkyl group, substituted alkyl group, or alicyclic hydrocarbon group. At least one hydrogen atom of these groups may be replaced with at least one fluorine atom. Of these examples, a more preferable one is —C(=O)—O—CR$^7$R$^8$— where each of $R^7$ and $R^8$ is independently a hydrogen atom or lower alkyl group.

A structure of the fluorine-containing polymer compound is derived from the polymerizable double-bond containing group and is represented by formula (19),

(19)

where each of $R^4$ and $R^6$ is independently a hydrogen atom, alkyl group or alicyclic hydrocarbon group, and $R^5$ represents a hydrogen atom, cyano group, halogen atom, or alkyl group.

This alkyl group may be a substituted or unsubstituted one having a carbon atom number of 1-4. Examples of the alkyl group include methyl group, ethyl group, n-propyl group, isopropyl group, n-butyl group, isobutyl group, sec-butyl group, and tert-butyl group. The alkyl group may have a substituent that is a $C_1$-$C_4$ alkoxy group, halogen atom, acyl group, acyloxy group, cyano group, hydroxy group, carboxyl group, alkoxycarbonyl group, or nitro group.

The polymerizable double-bond containing group $R^1$ of the fluorine-containing compound represented by formula (1) may be (a) a $C_2$-$C_{10}$ alkenyl group, such as vinyl group, allyl group, isopropenyl group, 1-propenyl group, 1-butenyl group, 1-pentenyl group, 1-methyl-1-propenyl group, 1-methyl-1-butenyl group, 2-methyl-1-butenyl group, 1-methyl-1-pentenyl group, 2-methyl-1-pentenyl group, 3-methyl-1-pentenyl group, and 4-methyl-1-pentenyl group; (b) a $C_2$-$C_{10}$ fluorine-containing alkenyl group, such as perfluoroallyl group, 3-trifluoromethyl-2-propenyl group, 1-perfluorobutenyl group, 1-perfluoropentenyl group, 1-trifluoromethyl-1- butenyl group, 2-trilfluoromethyl-1-butenyl group, 3-trifluoromethyl-1-butenyl group, and 4-trifluoromethyl-1-butenyl group; or (c) a $C_2$-$C_{10}$ alkenyl group having a substituent that is a substituted or unsubstituted phenyl group, such as 1-phenyl-1-propenyl group, 2-phenyl-1-propenyl group, 3-phenyl-1-propenyl group, 1-phenyl-1-butenyl group, 3-phenyl-1-butenyl group, and 4-phenyl-1-butenyl group; or (d) a $C_2$-$C_{10}$ alkenyl group having a substituent that is an alicyclic hydrocarbon group, cycloether group, lactone group, or an alicyclic hydrocarbon group that is a norbornene skeleton, norbornane skeleton, isobornyl skeleton, tricyclodecane skeleton, tetracyclododecane skeleton, adamantane skeleton, or the like.

As $R^4$, $R^5$ or $R^6$, a simple alicyclic hydrocarbon group or a combined alicyclic hydrocarbon group formed by simple alicyclic hydrocarbon groups that are combined together through carbon atoms may have a monocyclic or polycyclic structure. Specifically, these groups may have a monocyclo, bicyclo, tricyclo or tetracyclo structure of a carbon number of at least 5. The carbon number is preferably 6-30, more preferably 7-25. These alicyclic hydrocarbon groups may have substituents.

Examples of the alicyclic hydrocarbon group of $R^4$, $R^5$ or $R^6$ may be the same as those of that of $R^7$ or $R^8$ in the description of the linking group W.

In the structure represented by formula (9) of the fluorine-containing polymer compound, two of $R^4$, $R^5$ and $R^6$ may be combined together, thereby forming the following exemplary ring structure represented by formula (5),

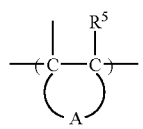

(5)

where $R^5$ represents a hydrogen atom, cyano group, halogen atom, or alkyl group; and A represents a group containing two carbon atoms C—C combined together, for forming an alicyclic structure.

This alicyclic structure may have a $C_3$-$C_{10}$ monocyclic or polycyclic structure, such as cyclopentane, cyclohexane, cycloheptane, norbornane, or a structure in which at least one hydrogen atom of these structures has been replaced with at least one lower alkyl or lower fluoroalkyl group.

Furthermore, the polymerizable double-bond containing group $R^1$ of the fluorine-containing compound may have a structure represented by the following formula (5-1) or (5-2) or a structure of vinylphenyl group,

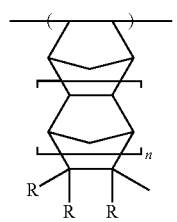

(5-1)

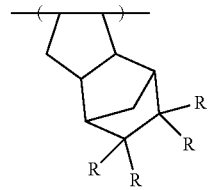

(5-2)

where formulas (5-1) and (5-2) are shown in the form of repeating unit after cleavage of the double bond, each of R's independently represents a hydrogen atom, halogen atom, or cyano group, and n represents an integer of 1-4.

The polymerizable double-bond containing group $R^1$ of the fluorine-containing compound is preferably a structure represented by $CH_2=CH-$, $CH_2=C(CH_3)-$, $CH_2=C(CF_3)-$ or $CH_2=C(CH_2OH)-$, or a structure represented by one of the following formulas (5-3) to (5-6),

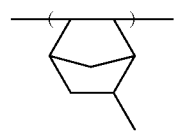

(5-3)

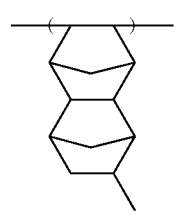

(5-4)

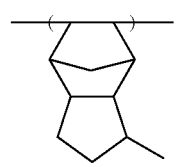

(5-5)

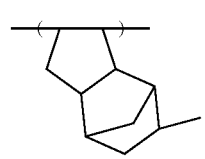

(5-6)

where formulas (5-3) to (5-6) are shown in repeating unit after cleavage of the double bond, or a group derived from a vinylphenyl group. Of these, $CH_2=CH-$, $CH_2=C(CH_3)-$, and $CH_2=C(CF_3)-$ are more preferable, and $CH_2=C(CH_3)-$ is still more preferable.

It is preferable that the following partial structure (19-1)

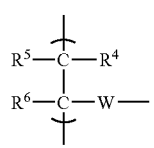

(19-1)

where all of the symbols are defined as in formula (2), contained in the repeating unit (a) represented by formula (2) has a structure obtained by cleavage of the polymerizable double-bond of a group selected from vinyloxy group, allyloxy group, acryloyloxy group, methacryloyloxy group, α,α,α-trifluoroacryloyloxy group, norbornoyloxy group, and vinylphenoxy group, which are respectively shown as follows.

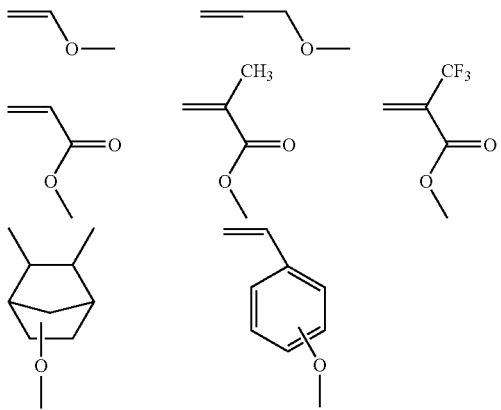

The fluorine-containing unsaturated carboxylic acid represented by formula (1) may have a formula selected from the following most preferable exemplary formulas,

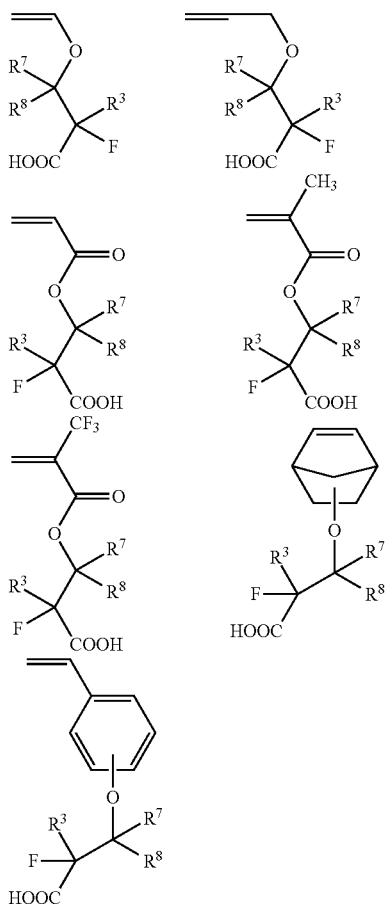

wherein $R^3$ represents a fluorine atom or trifluoromethyl group, $R^7$ represents a hydrogen atom or a straight-chain, branched or cyclic alkyl or fluoroalkyl group, $R^8$ represents a straight-chain, branched or cyclic alkyl or fluoroalkyl group, and $R^7$ and $R^8$ may be combined to form a ring.

In the above formulas, $R^3$ is particularly preferably a fluorine atom. The alkyl or fluoroalkyl group of $R^7$ and $R^8$ is preferably a lower alkyl or lower fluoroalkyl group. It is preferable that the alkyl group is a cyclic alkyl group. It is preferable that $R^7$ represents a hydrogen atom. It is particularly preferable that $R^3$ represents a fluorine atom, $R^7$ represents a hydrogen atom or lower alkyl group, and $R^8$ represents a lower alkyl group. It is also preferable that $R^3$ represents a fluorine atom, and $R^7$ and $R^8$ are bonded together to form a lower alicyclic hydrocarbon group.

In the alkali-soluble resin component, the repeating unit (a) is in preferably 1-99 mol %, more preferably 3-90 mol %, particularly preferably 5-80 mol %, the most preferably 10-70 mol %, based on the total mole number of all the repeating units of the alkali-soluble resin component. With 1 mol % or more of the repeating unit (a), it is possible to obtain solubility due to containment of the repeating unit (a). With 99 mol % or less of the repeating unit (a), a balance between the repeating unit (a) and other repeating units is good.

The fluorine-containing polymer compound may contain only one type of the repeating unit (a) or a mixture of at least two types of the repeating unit (a).

Repeating Unit (b)

The repeating unit (b) having an alcoholic hydroxy group at its side chain is described in detail, as follows.

The alcoholic hydroxy group of the repeating unit (b) contained in the alkali-soluble resin component in the negative-type resist composition of the present invention is an almost neutral hydroxy group and normally is not involved in dissolving the resin in alkali solution. It refers to a hydroxy group having a function of making the resin component, which has originally been soluble in alkali solution, insoluble therein, through a crosslinking by a reaction, in which the hydroxy group is involved, to form an ester bond, ether bond, ureide bond, or the like.

A chain skeleton of the repeating unit (b), derived from a polymerizable double bond, may be the same as one of basic skeletons of acrylate polymers, novolac resins, vinyl resins, allyl resins, so-called alicyclic polymerizable double-bond series resins, and the like. It is possible to produce the alkali-soluble resin component by copolymerizing a monomer for producing the repeating unit (a) with a monomer for producing the repeating unit (b).

The repeating unit (b) may be represented by the following formula (6),

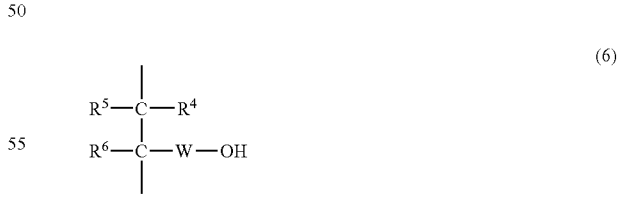

(6)

wherein each of $R^4$, $R^5$ and $R^6$ independently represents a hydrogen atom, fluorine atom or monovalent organic group, and at least two of $R^4$, $R^5$ and $R^6$ may be combined to form a ring, and W represents a bivalent linking group. Since descriptions of these signs (i.e., $R^4$, $R^5$, $R^6$ and W) correspond to those in formulas (1) and (2), they are not repeated herein.

It is preferable that the repeating unit (b) represented by formula (6) is a repeating unit represented by formula (7), for improving development property of the resist composition,

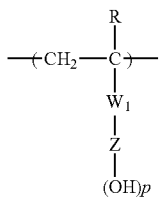

(7)

wherein R represents a hydrogen atom, alkyl group, halogenated alkyl group, halogen atom, or hydroxyalkyl group;

$W_1$ represents a single bond, —C(=O)—O—, or —O—;

Z represents an alicyclic hydrocarbon group, an aliphatic acyclic hydrocarbon group, or an organic group formed of a combination of these groups, each of these groups having a valence of "p+1";

p represents an integer of 0-3; and

R represents a hydroxyalkyl group when p=0.

In R of formula (7), each of the alkyl group and an alkyl group moiety contained in the halogenated alkyl group and the hydroxyalkyl group may be an alkyl group having a carbon number of 10 or less, preferably a $C_1$-$C_4$ lower alkyl group or its derivative.

The hydroxyalkyl group may be a straight-chain or branched hydroxyalkyl group having a carbon atom number of 10 or less, preferably a $C_1$-$C_8$ hydroxyalkyl group, more preferably hydroxymethyl or hydroxyethyl group. Although there is no particular limitation in terms of the number of hydroxy groups and their bonding positions in the hydroxyalkyl group, it is preferable that one hydroxy group is bonded to the terminal of the alkyl group.

Examples of the repeating unit (b) represented by formula (7), in which R represents a hydroxyalkyl group, include a repeating unit derived from an alkyl α-(hydroxyalkyl)acrylate and a repeating unit derived from a hydroxyalkyl (α-alkyl)acrylate.

Of these, an alkyl α-(hydroxymethyl)acrylate and an alkyl α-(hydroxyethyl)acrylate are preferable. Furthermore, in terms of crosslinking efficiency and film density improvement, a repeating unit derived from ethyl α-(hydroxymethyl) acrylate or methyl α-(hydroxymethyl)acrylate is preferable.

The alicyclic hydrocarbon group as Z in formula (7) may have a monocyclic or polycyclic structure, but it is preferably a polycyclic group. It is preferably saturated. The number of carbons in the alicyclic hydrocarbon group is preferably 5 to 15.

The aliphatic hydrocarbon group as Z in formula (7) may be a residue obtained by removing hydrogen atoms that are "p" in number from a saturated hydrocarbon group that is branched or not. This residue may have a halogen atom(s) as a substituent(s). It is preferable that "p" is 1. The aliphatic hydrocarbon group may be a $C_1$-$C_{10}$ alkyl group, preferably $C_1$-$C_8$ alkyl group, more preferably ethyl group or methyl group.

The halogenated alkyl group as Z in formula (7) may be a lower alkyl group (preferably ethyl or methyl group) of which hydrogen atoms have partially or entirely been replaced with a halogen atom(s) (preferably fluorine atom(s)).

Depending on the purpose of adjusting properties of the resist composition, the repeating unit (b) may suitably be selected from the above-mentioned ones. For example, the repeating unit (b) is preferably one represented by the following formula (7-1), for obtaining a wide exposure margin in the line pattern formation by under exposure,

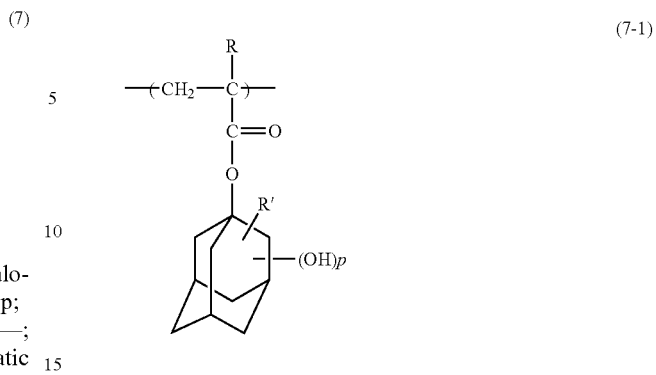

(7-1)

wherein R represents a hydrogen atom, alkyl group, halogen atom, or halogenated alkyl group; R' represents a hydrogen atom, alkyl group, or $C_1$-$C_5$ alkoxy group; and p is an integer of 1-3, preferably 1.

The alkyl group as R in formula (7-1) may be a $C_1$-$C_5$ alkyl group, such as methyl group, ethyl group, propyl group, isopropyl group, n-butyl group, isobutyl group, tert-butyl group, pentyl group, isopentyl group, or neopentyl group. It is preferably a lower alkyl group, more preferably a methyl group.

The alkoxy group as R' in formula (7-1) is a residue in which an oxygen atom is bonded to the above alkyl group as R. It is straight-chain or branched, and its carbon number is preferably 1-5, more preferably 1-3.

In formula (7-1), the bonding position of the alcoholic hydroxy group is not particularly limited, but is preferably C3-position of the adamantyl group.

Besides formula (7-1), specific preferable examples of the repeating unit (b) represented by formula (7) include those represented by the following formulas,

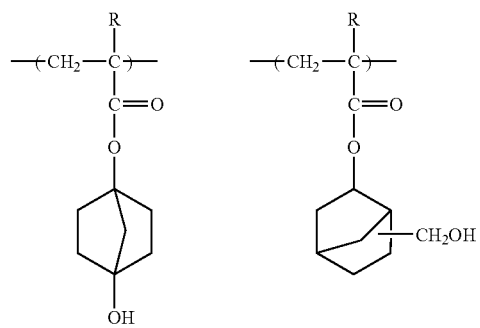

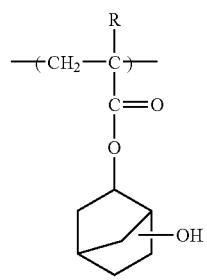

-continued

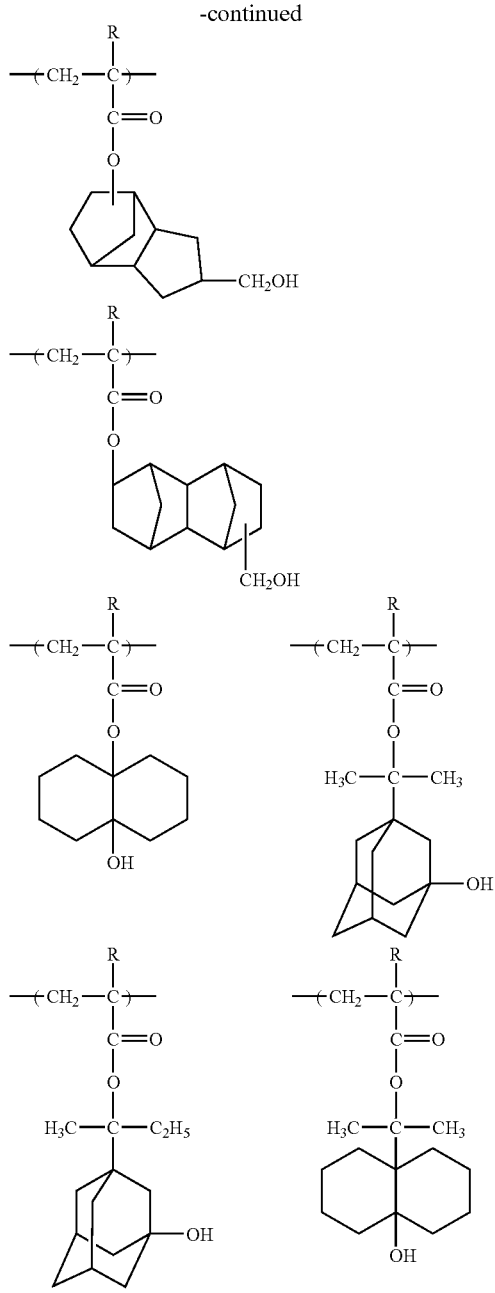

where each of R's represents a hydrogen atom or methyl group.

Other examples of the repeating unit (b) having an alcoholic hydroxy group at its side chain are mentioned, as follows.

For example, they include alkyl acrylates or methacrylates, such as 2-hydroxyethyl acrylate or methacrylate, 4-hydroxybutyl acrylate or methacrylate, 5-hydroxypentyl acrylate or methacrylate, 2,2-dimethyl-3-hydroxypropyl acrylate or methacrylate, trimethylolpropane monoacrylate or methacrylate, pentaerythritol monoacrylate or methacrylate, and 2-hydroxypropyl acrylate or methacrylate; acrylates or methacrylates containing ethylene glycol, propylene glycol, and tetramethylene glycol; and 3-oxocyclohexyl acrylate or methacrylate.

Furthermore, they include vinyl ethers containing an alcoholic hydroxy group, such as hydroxymethyl vinyl ether, 2-hydroxyethyl vinyl ether, 3-hydroxypropyl vinyl ether, 4-hydroxybutyl vinyl ether, 5-hydroxypentyl vinyl ether, 6-hydroxyhexyl vinyl ether, diethylene glycol monovinyl ether, polyethylene glycol monovinyl ether, and 1,4-cyclohexanedimethanol vinyl ether.

Furthermore, they include allyl ethers containing an alcoholic hydroxy group, such as alkylene glycol monoallyl ethers (e.g., ethylene glycol monoallyl ether, propylene glycol monoallyl ether, diethylene glycol monoallyl ether, polyethylene glycol monoallyl ether, and hydroxybutyl allyl ether), and allyl ethers of polyhydric alcohols (e.g., allyl alcohol and glycerol monoallyl ether).

Furthermore, they include unsaturated amides, such as N-hydroxymethyl acrylamide or methacrylamide, N-hydroxyethyl acrylamide or methacrylamide, N-hydroxyethyl-N-methyl acrylamide or methacrylamide, N-methylolacrylamide, and N-methylolmethacrylamide.

The repeating unit (b) may be used singly or in combination of at least two kinds.

The content of the repeating unit (b) in the alkali-soluble resin component is preferably 1-90 mol %, more preferably 3-85 mol %, still more preferably 5-80 mol %, based on the total mole number of all the repeating units of the alkali-soluble resin component. It is possible to obtain a sufficient crosslinking effect if it is 1 mol % or greater. It is possible to have a good balance with the other repeating units if it is 90 mol % or less.

Repeating Unit (c)

The fluorine-containing polymer compound of the present invention is obtained by homopolymerization of the fluorine-containing unsaturated carboxylic acid represented by formula (1) or by its copolymerization with at least one polymerizable monomer (comonomer). In this polymerization, cleavage of the C—C double bond of the polymerizable double-bond containing group $R^1$ of the fluorine-containing unsaturated carboxylic acid occurs to form a skeleton of the fluorine-containing polymer compound, but the rest of the structure of the fluorine-containing unsaturated carboxylic acid does not change.

Besides the repeating unit (a) represented by formula (2), the fluorine-containing polymer compound can contain various repeating units for the purpose of adjusting dry etching resistance, standard developing solution suitability, adhesion to substrate, resist profile, and general characteristics (e.g., resolution, heat resistance and sensitivity) necessary for resist.

Besides the repeating units (a) and (b), the alkali-soluble resin component may contain various repeating units. Such repeating units may be those corresponding to the after-mentioned monomers, but are not limited to those. By containing such repeating units, it is possible to achieve fine adjustments of qualities necessary for the resin, particularly (1) solubility in coating solvent, (2) film forming property (glass transition point), (3) alkali development property, (4) film decrease upon alkali development (hydrophilic or hydrophobic property and alkali-soluble group selection), (5) adhesion of the unexposed portion to substrate, and (6) dry etching resistance.

Repeating unit (c) may be derived from an acrylate or methacrylate containing a monocyclic or polycyclic, lactone-ring containing group. Another repeating unit (d) may be derived from a monomer selected from the following monomers. Herein, a repeating unit that belongs to both of the repeating units (c) and (d) is defined as being repeating unit (c). Examples of other comonomers copolymerizable with the fluorine-containing unsaturated carboxylic acid to produce repeating units (c) and (d) include acrylates, fluorine-containing acrylates, methacrylates, fluorine-containing methacrylates, styrene compounds, fluorine-containing styrene compounds, vinyl ethers, fluorine-containing vinyl ethers, allyl ethers, fluorine-containing allyl ethers, acrylamides, methacrylamides, vinyl esters, allyl esters, olefins, fluorine-containing olefins, norbornene compounds, fluorine-containing norbornene compounds, sulfur dioxide, and vinyl silanes. At least one monomer selected from these may be copolymerized with the fluorine-containing unsaturated carboxylic acid.

When the monocyclic or polycyclic, lactone-ring containing group of repeating unit (c) is used for forming a resist film, it is effective for improving adhesion of the resist film to substrate, improving hydrophilicity (i.e., affinity for the developing solution), and preventing swelling. Repeating unit (c) is not particularly limited, as long as it has a lactone ring, which contains a ring of atoms in which an ester structure (—O—C(O)—) forms part of the ring.

A repeating unit having a lactone group is preferably an acrylate, methacrylate or α,α,α-trifluoroacrylate containing a lactone group, more preferably an acrylate or methacrylate containing a lactone group. This lactone group may be any group containing a lactone structure. It is preferably a group containing a five to seven-membered lactone structure. It is preferably a group having a ring-fused structure (e.g., bicyclo structure and spiro structure) formed by a combination of another ring structure with a five to seven-membered lactone structure. By containing a lactone ring, the resulting resist is improved in line edge roughness and development defect.

The above lactone group may be selected from the structures represented by the following formulas (8-1) and (8-2),

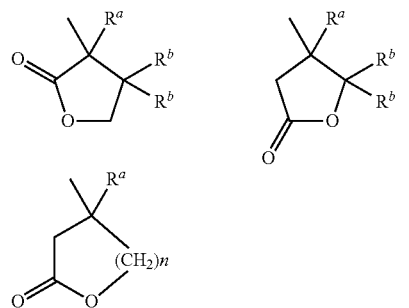

(8-1)

where $R^a$ represents a $C_1$-$C_4$ alkyl group or perfluoroalkyl group, each of $R^b$ independently represents a hydrogen atom, a $C_1$-$C_4$ alkyl group or perfluoroalkyl group, a hydroxy group, a carboxyl group, an alkyloxycarbonyl group, an alkoxy group or the like, and n represents an integer of 1-4,

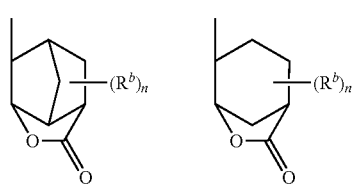

(8-2)

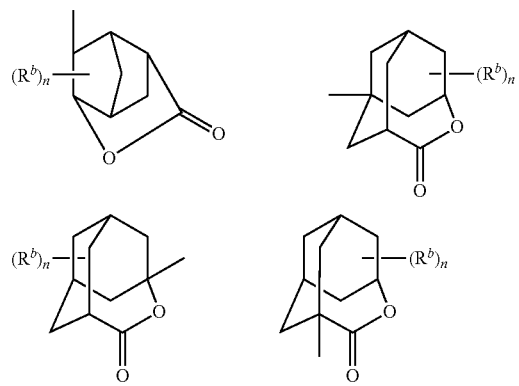

where each of $R^b$ independently represents a hydrogen atom, a $C_1$-$C_4$ alkyl group or perfluoroalkyl group, a hydroxy group, a carboxyl group, an alkyloxycarbonyl group, an alkoxy group or the like, and n represents an integer of 1-4.

Specific examples of the lactone group include the following formulas (9-1) to (9-6).

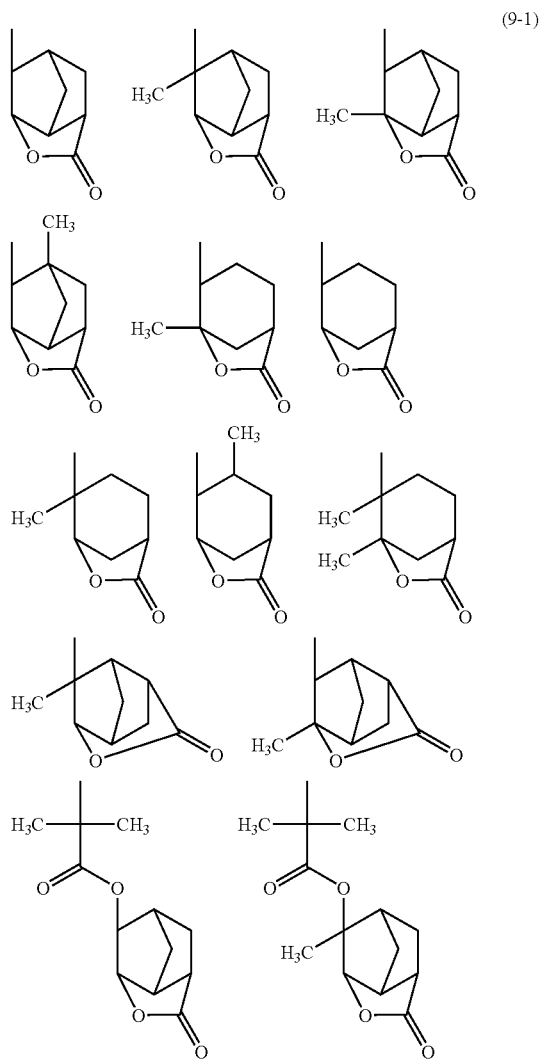

(9-1)

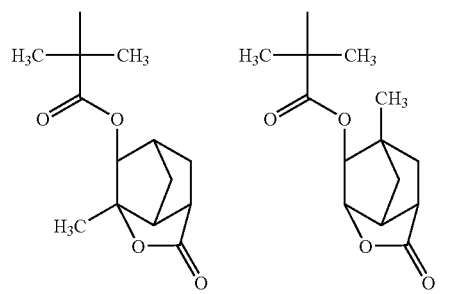
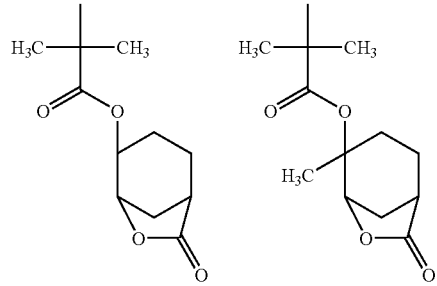
(9-2)
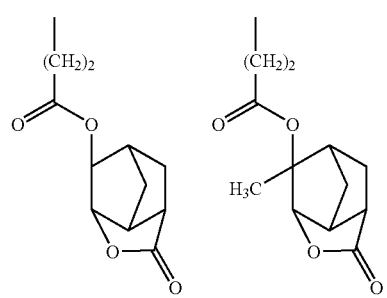
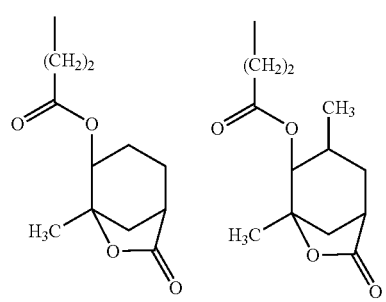
(9-3)
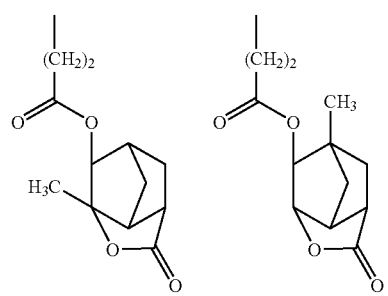
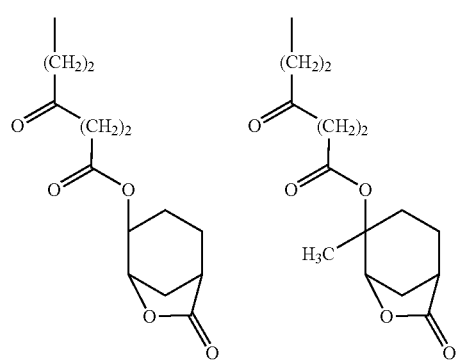
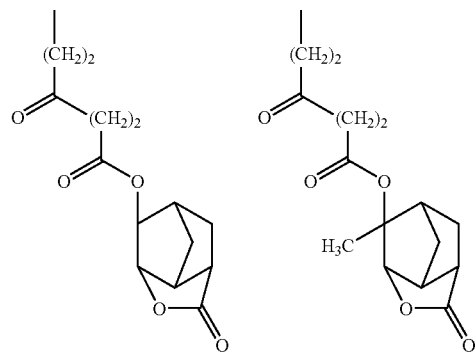
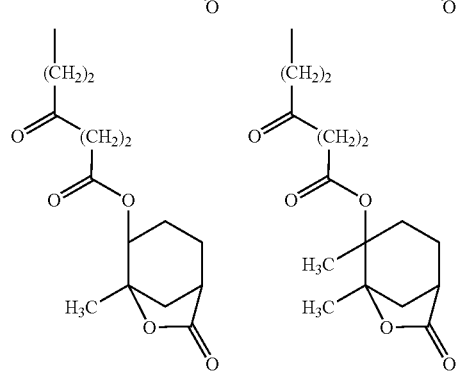
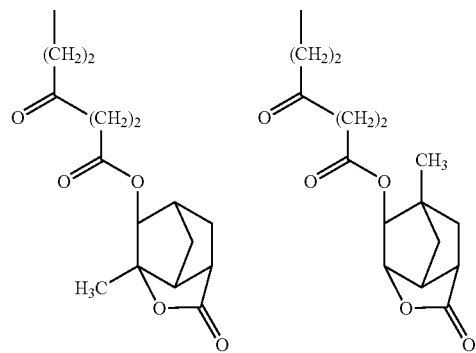
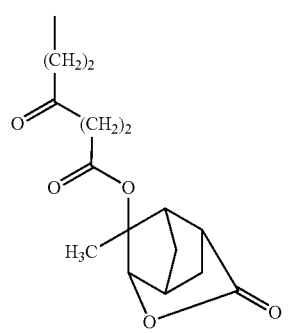

-continued
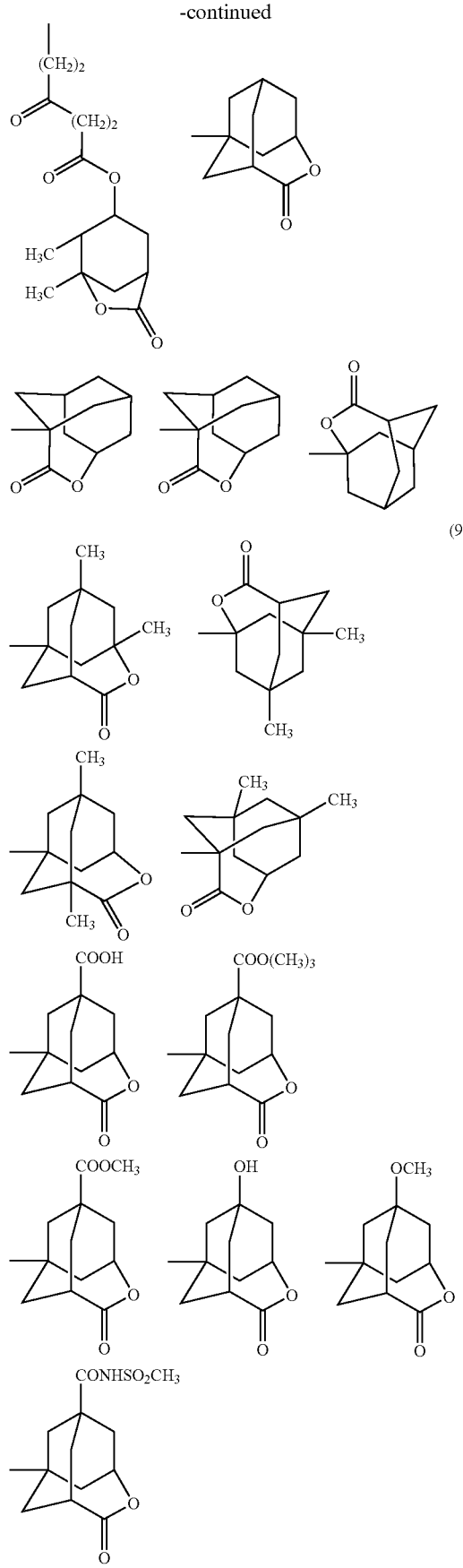
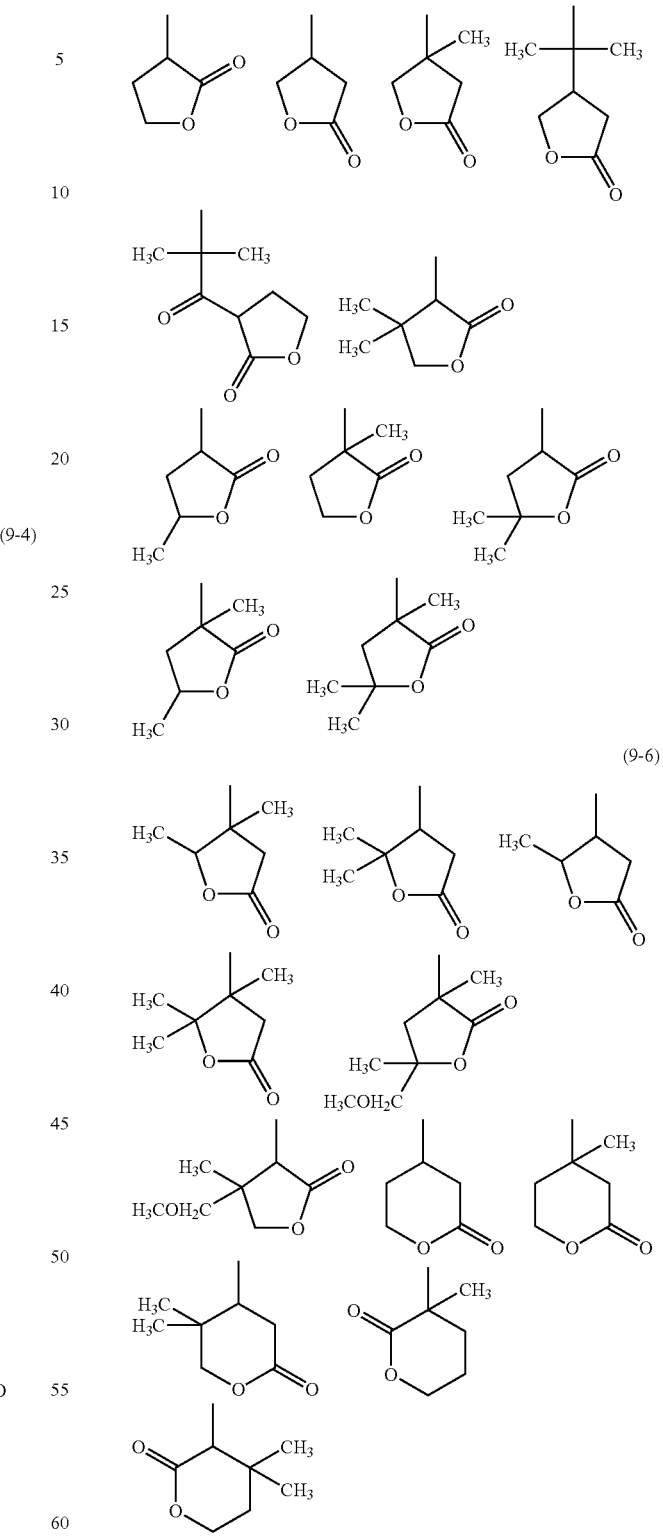
In the formulas (9-1) to (9-6), methyl groups (CH$_3$) may independently be replaced with ethyl groups.
In the polymerization, a lactone-ring containing comonomer for forming repeating unit (c) may be used singly or in a mixture of at least two kinds.

The content of repeating unit (c) in the alkali-soluble resin component is preferably 10-90 mol %, more preferably 20-90 mol %, particularly preferably 40-90 mol %, the most preferably 45-85 mol %, based on all the repeating units of the alkali-soluble resin component. With 10 mol % or more of the repeating unit (c), it is possible to obtain advantageous effects, such as adhesion, due to containment of the repeating unit (c). With 90 mol % or less of the repeating unit (c), it is possible to maintain a good balance between the repeating unit (c) and other repeating units.

Repeating Unit (d)

The alkali-soluble resin component may contain repeating unit (d), which may be derived from a comonomer selected from acrylates and mathacrylates. These acrylates and methacrylates are not particularly limited with respect to their ester moiety. Their examples include alkyl esters of acrylic acid or methacrylic acid, such as methyl acrylate or methacrylate, ethyl acrylate or methacrylate, n-propyl acrylate or methacrylate, isopropyl acrylate or methacrylate, n-butyl acrylate or methacrylate, isobutyl acrylate or methacrylate, tert-butyl acrylate or methacrylate, amyl acrylate or methacrylate, n-hexyl acrylate or methacrylate, n-octyl acrylate or methacrylate, 2-ethylhexyl acrylate or methacrylate, benzyl acrylate or methacrylate, chlorobenzyl acrylate or methacrylate, octyl acrylate or methacrylate, furfuryl acrylate or methacrylate, tetrahydrofurfuryl acrylate or methacrylate, lauryl acrylate or methacrylate; 3-oxocyclohexylacrylate or methacrylate, adamantyl acrylate or methacrylate, alkyladamantyl acrylate or methacrylate, cyclohexyl acrylate or methacrylate, tricyclodecanyl acrylate or methacrylate, and acrylates or methacrylates containing a ring structure (e.g., norbornene ring); and the above-mentioned acrylates containing a trifluoromethyl group or cyano group at α-position.

The fluorine-containing acrylates or methacrylates usable in the present invention contain fluorine at their ester moiety and may have a cyano group at their α-position.

It is possible to use without a particular limitation fluorine-containing acrylates or methacrylates in which a part of the ester moiety of the above-mentioned acrylates or methacrylates has been fluorinated. In other words, they are acrylates or methacrylates having at their ester moiety a fluorine-containing alkyl group or a fluorine-containing ring structure (e.g., fluorine-containing benzene ring, fluorine-containing cyclopentane ring, fluorine-containing cyclohexane ring, fluorine-containing cycloheptane ring, fluorine-containing norbornel group, and fluorine-containing adamantyl group) in which at least one hydrogen at their ring carbon(s) has been replaced with at least one fluorine atom or fluorine-containing alkyl group (e.g., trifluoromethyl group). Furthermore, it is also possible to use acrylates or methacrylates having at their ester moiety a fluorine-containing tert-butyl ester or a cyclohexyl group or norbornyl group containing a hexafluoroisopropanol group substituted.

Repeating unit (d) may be derived from a comonomer selected from vinyl ethers or allyl ethers having a $C_1$-$C_{30}$ alkyl group, fluoroalkyl group or alicyclic hydrocarbon group as a substituent. These groups preferably contain a halogen atom, hydroxy group, amino group, aryl group, alkyl group or alicyclic hydrocarbon group as a substituent. The vinyl ethers and allyl ethers are exemplified, as follows.

Specific examples of alkyl vinyl ether include methyl vinyl ether, ethyl vinyl ether, propyl vinyl ether, isopropyl vinyl ether, butyl vinyl ether, isobutyl vinyl ether, sec-butyl vinyl ether, tert-butyl vinyl ether, pentyl vinyl ether, hexyl vinyl ether, octyl vinyl ether, decyl vinyl ether, and dodecyl vinyl ether. Those of cyclic vinyl ether include cyclopentyl vinyl ether, cyclohexyl vinyl ether, norbornyl vinyl ether, and adamantyl vinyl ether. Those of perfluoroalkyl vinyl ether include perfluoromethyl vinyl ether, perfluoroethyl vinyl ether, perfluoropropyl vinyl ether, perfluoroisopropyl vinyl ether, perfluorobutyl vinyl ether, perfluoroisobutyl vinyl ether, perfluoro-sec-butyl vinyl ether, perfluoro-tert-butyl vinyl ether, perfluoropentyl vinyl ether, perfluorohexyl vinyl ether, perfluorooctyl vinyl ether, and perfluorododecyl vinyl ether. Further specific examples of vinyl ether include ethylhexyl vinyl ether, methoxyethyl vinyl ether, ethoxyethyl vinyl ether, chloroethyl vinyl ether, 1-methyl-2,2-dimethylpropyl vinyl ether, 2-ethylbutyl vinyl ether, diethylene glycol vinyl ether, dimethylaminoethyl vinyl ether, diethylaminoethyl vinyl ether, butylaminoethyl vinyl ether, benzyl vinyl ether, and tetrahydrofurfuryl vinyl ether.

Specific examples of allyl ethers include methyl allyl ether, ethyl allyl ether, propyl allyl ether, butyl allyl ether, benzyl allyl ether, and cyclohexyl allyl ether.

Further examples include epoxy group-containing vinyl ethers and allyl ethers. As a β-ketoester group containing vinyl ether or allyl ether, it is possible to cite allyl acetoacetate. Furthermore, it is possible to cite silicon-containing vinyl ethers having a hydrolyzable group, such as trimethoxysilyl vinyl ether.

Specific examples of allyl esters include allyl acetate, allyl caproate, allyl caprylate, allyl laurate, allyl palmitate, allyl stearate, allyl benzoate, allyl acetoacetate, and allyl lactate.

Specific examples of vinyl esters include vinyl butyrate, vinyl isobutyrate, vinyl trimethylacetate, vinyl diethylacetate, vinyl valerate, vinyl caproate, vinyl chloroacetate, vinyl dichloroacetate, vinyl methoxyacetate, vinyl butoxyacetate, vinyl acetoacetate, vinyl lactate, vinyl β-phenylbutyrate, and vinyl cyclohexylcarboxylate.

Further examples include dialkyl itaconates, such as dimethyl itaconate, diethyl itaconate and dibutyl itaconate; dialkyl fumarates or monoalkyl fumarates, such as dibutyl fumarate; and alkyl vinyl acetates such as ethyl vinyl acetate.

Specific examples of olefins include ethylene, propylene and cyclohexene. Those of fluorine-containing olefins include vinyl fluoride, vinylidene fluoride, trifluoroethylene, chlorotrifluoroethylene, tetrafluoroethylene, hexafluoropropylene, hexafluoroisobutene, and octafluorocyclopentene.

A styrene compound usable in the present invention is a compound in which a vinyl group is bonded to an aromatic ring. Its specific examples include styrene, m- or p-hydroxystyrene, m- or p-methoxystyrene, m- or p-ethoxystyrene, m- or p-propoxystyrene, m- or p-isopropoxystyrene, m- or p-butoxystyrene, m- or p-tert-butoxystyrene, m- or p-(1-ethoxyethoxy)styrene, m- or p-(1-ethoxypropoxy)styrene, m- or p-(1-isobutoxyethoxy)styrene, m- or p-(2-tetrahydropyranyloxy)styrene, m- or p-tert-butoxycarbonyloxystyrene, m- or p-acetoxystyrene, m- or p-propionyloxystyrene, m- or p-pivaloyloxystyrene, m- or p-benzoyloxystyrene, m- or p-mesyloxystyrene, m- or p-phenylsulfonyloxystyrene, and m- or p-tosyloxystyrene. These styrene compounds may have at their α-position a halogen atom, alkyl group or fluorine-containing alkyl group.

In the case of introducing the structure of a hydroxystyrene compound into the fluorine-containing polymer compound, for example, p-butoxycarbonyloxystyrene is copolymerized with the fluorine-containing unsaturated carboxylic acid, and then the butoxycarbonyl moiety may be converted into a hydroxy group.

Furthermore, it is possible to use a vinyl naphthalene derivative or iospropenyl naphthalene derivative, such as 2-hydroxy-1-vinyl naphthalene, 3-hydroxy-1-vinyl naphthalene, 4-hydroxy-1-vinyl naphthalene, 5-hydroxy-1-vinyl naphthalene, 6-hydroxy-1-vinyl naphthalene, 7-hydroxy-1-vinyl naphthalene, 8-hydroxy-1-vinyl naphthalene, 2-hydroxy-1-isopropenyl naphthalene, 3-hydroxy-1-isopropenyl naphthalene, 4-hydroxy-1-isopropenyl naphthalene, 5-hydroxy-1-isopropenyl naphthalene, 6-hydroxy-1-isopropenyl naphthalene, 7-hydroxy-1-isopropenyl naphthalene, 8-hydroxy-1-isopropenyl naphthalene, 2-carboxy-1-vinyl naphthalene, 3-carboxy-1-vinyl naphthalene, 4-carboxy-1-vinyl naphthalene, 5-carboxy-1-vinyl naphthalene, 6-carboxy-1-vinyl naphthalene, 7-carboxy-1-vinyl naphthalene, and 8-carboxy-1-vinyl naphthalene.

The norbornene compounds or fluorine-containing norbornene compounds or compounds analogous to these are norbornene monomers having a monocyclic or polycyclic structure. In the invention, it is preferable to use a norbornene compound or fluorine-containing norbornene compound obtained by Diels Alder addition reaction between an unsaturated compound (e.g., fluorine-containing olefins, allyl alcohol, fluorine-containing allyl alcohols, acrylic acid, α-fluoroacrylic acid, methacrylic acid, vinyl esters, fluorine-containing vinyl esters, and acrylates, methacrylates, fluorine-containing acrylates and fluorine-containing methacrylates, which are exemplified hereinbefore) and cyclopentadiene or cyclohexadiene.

Specific examples of the acrylamide or methacryloamides include unsaturated amides such as acrylamide, methacrylamide, N-alkylacrylamide or methacryloamide, where alkyl group is $C_1$-$C_{10}$ one (e.g., methyl group, ethyl group, propyl group, butyl group, tert-butyl group, heptyl group, octyl group, cyclohexyl group, and hydroxyethyl group), N,N-dialkylacrylamide or acryloamide, where alkyl group is $C_1$-$C_{10}$ one (e.g., methyl group, ethyl group, butyl group, isobutyl group, ethylhexyl group, and cyclohexyl group).

Further examples of other comonomers include unsaturated carboxylic acids, such as acrylic acid, methacrylic acid, vinylacetic acid, vinylsulfonic acid, maleic acid, fumaric acid, crotonic acid, itaconic acid, and cinnamic acid, carboxyl-containing unsaturated carboxylates, such as 3-carboxypropyl(meth)acrylate and 4-carboxybutyl(meth)acrylate, and maleimide, acrylonitrile, methacrylonitrile, maleilonitrile, an alkoxysilyl group-containing vinyl silane, and allyloxyethanol.

To conduct a copolymerization for producing the fluorine-containing polymer compound represented by formula (2), it is preferable to use at least one of the above-explained acrylates, fluorine-containing acrylates, methacrylates, fluorine-containing methacrylates, styrene compounds, and fluorine-containing styrene compounds.

Other comonomers are not particularly limited, as long as they are copolymerizable with the fluorine-containing unsaturated carboxylic acid represented by formula (1). For exposure with a high energy ray of 300 nm or shorter, it is preferable that they contain an alkyl group, fluorine-containing alkyl group, monocyclic or polycyclic aliphatic hydrocarbon group, monocyclic or polycyclic fluorine-containing aliphatic hydrocarbon group, monocyclic or polycyclic ether group, or monocyclic or polycyclic lactone group. Furthermore, it is preferable that they are free from an aromatic ring and a multiple bond other than a polymerizable double bond for forming a chain skeleton of the fluorine-containing polymer compound.

Repeating unit (d) may be used singly or in combination of at least two kinds.

Repeating unit (d) is not essential for the alkali-soluble resin component. In the case of containing repeating unit (d) in the alkali-soluble resin component, the content of repeating unit (d) in the alkali-soluble resin component is preferably 70 mol % or less, more preferably 40 mol % or less, still more preferably 30 mol % or less, based on the total mole number of all the repeating units of the alkali-soluble resin component. It is possible to obtain various advantageous effects by containing repeating unit (d).

It is preferable that the alkali-soluble resin component is a copolymer containing repeating units (a) and (b) as main components. Herein, the term of "main components" means that the total mole number of repeating units (a) and (b) is 50 mol % or greater, preferably 70 mol % or greater, more preferably 80 mol % or greater, based on the total mole number of all the repeating units of the alkali-soluble resin component. The alkali-soluble resin component may be a copolymer consisting of repeating units (a) and (b).

The alkali-soluble resin component may be 1,000-1,000,000, preferably 2,000-500,000, more preferably 2,000-100,000, in weight average molecular weight determined by gel permeation chromatography (GPC). If it is less than 1,000, the resist film may become insufficient in strength. If it is greater than 1,000,000, solubility in solvent may become too low. With this, it may become difficult to obtain a flat resist film. Dispersibility (Mw/Mn where Mw represents weight average molecular weight, and Mn represents number average molecular weight) is preferably 1.01-5.00, more preferably 1.01-4.00, particularly preferably 1.01-3.00, the most preferably 1.10-2.50.

The alkali-soluble resin component can be obtained, for example, by an ordinary process through radical polymerization of monomers for obtaining respective repeating units.

In the preparation of the negative-type resist composition of the present invention, the alkali-soluble resin component is used singly or in combination of at least two kinds. Furthermore, it is possible to add other polymer compounds (e.g., hydroxystyrene resin, novolac resin, and acrylic resin) to the alkali-soluble resin component. In this case, the content of the alkali-soluble resin component is preferably 50 wt % or greater, more preferably 70 wt % or greater, still more preferably 80 wt % or greater, the most preferably 100 wt %, based on the total weight of the alkali-soluble resin component and other polymer components.

Process for Producing Fluorine-Containing Polymer Compound

The process for producing the fluorine-containing polymer compound is not particularly limited, as long as it is one generally used. It is preferable to use radical polymerization or ion polymerization. In some cases, it is also possible to use coordination anion polymerization, living anion polymerization, cation polymerization, ring-opening metathesis polymerization, vinylene polymerization or vinyl addition polymerization.

The radical polymerization may be conducted by a known polymerization method, such as bulk polymerization, solution polymerization, suspension polymerization or emulsion polymerization, in the presence of a radical polymerization initiator or radical initiating source, with a batch-wise, half-continuous or continuous operation.

The radical polymerization initiator is not particularly limited. As its examples, azo compounds, peroxide compounds and redox compounds are cited. In particular, preferable examples include azobisbutyronitrile, t-butylperoxypivalate, di-t-butylperoxide, i-butyrylperoxide, lauroylperoxide, succinic acid peroxide, dicinnamylperoxide, di-n-propylperoxydicarbonate, t-butylperoxyallyl monocarbonate, benzoyl peroxide, hydrogen peroxide, and ammonium persulfate.

The reaction vessel used in the polymerization reaction is not particularly limited. Furthermore, a polymerization solvent may be used in the polymerization reaction. As the polymerization solvent, one that does not interfere with the radical polymerization is preferable. Representative ones are ester solvents such as ethyl acetate and n-butyl acetate; ketone solvents such as acetone and methyl isobutyl ketone; hydrocarbon solvents such as toluene and cyclohexane; and alcohol solvents such as methanol, isopropyl alcohol and ethylene glycol monomethyl ether. Furthermore, it is also possible to use solvents such as water, ethers, cyclic ethers, fluorohydrocarbons, and aromatics. These solvents can be used singly or in combination of at least two types. Furthermore, it may be accompanied in use with a molecular weight adjusting agent such as mercaptan. The reaction temperature of the polymerization reaction is suitably changed, depending on the radical polymerization initiator or radical polymerization initiating source. In general, 20-200° C. is preferable. In particular, 30-140° C. is preferable.

It is possible to remove organic solvent or water from the obtained solution or dispersion of the fluorine-containing polymer compound by reprecipitation, filtration, heating distillation under reduced pressure, or the like.

Fluorine-Containing Unsaturated Carboxylic Acid

Repeating unit (a) represented by formula (2) of the fluorine-containing polymer compound is formed by the production of a bivalent group through cleavage of the polymerizable double bond of the fluorine-containing unsaturated carboxylic acid (monomer) represented by formula (1). Thus, the above description in the section of "REPEATING UNIT (a)" with respect to the polymerizable double bond for forming the chain skeleton moiety, the group containing the polymerizable double bond, each organic group, the linking group W and the like corresponds directly to that of the fluorine-containing unsaturated carboxylic acid and therefore is not repeated herein.

The process for producing the fluorine-containing unsaturated carboxylic acid represented by formula (1) is not particularly limited. For example, it can be produced by a process represented by the following reaction formulas [1] to [3],

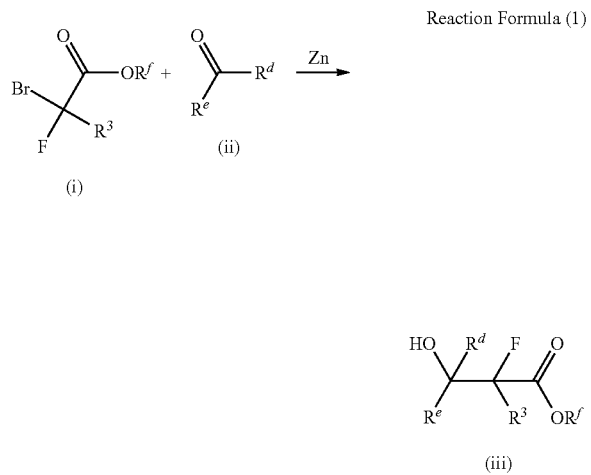

Reaction Formula (1)

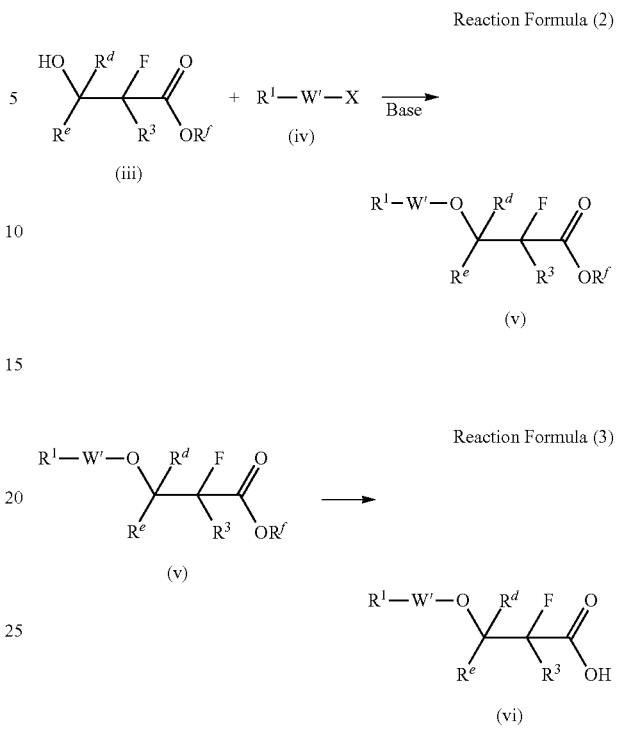

where $R^1$ and $R^3$ are defined as in formula (1); $R^d$ represents a hydrogen atom or monovalent organic group, and each of $R^e$ and $R^f$ independently represents a monovalent organic group; each of X and X' independently represents a halogen atom, trifluoromethanesulfonate group, $C_1$-$C_4$ alkylsulfonate group or arylsulfonate group; W' represents a bivalent linking group; and W'—O—$CR^dR^e$ corresponds to W in formula (1).

As each of $R^d$ and $R^e$ corresponds to $R^7$ or $R^8$, detailed description of $R^d$ and $R^e$ is the same as that of $R^7$ and $R^8$. The monovalent organic group as $R^d$, $R^e$ or $R^f$ is preferably a lower alkyl or fluoroalkyl group, such as methyl group, ethyl group, propyl group, butyl group, cyclopentyl group, cyclohexyl group, norbornyl group, adamantyl group, trifluoromethyl group, 2,2,2-trifluoroethyl group, 1-(trifluoromethyl)ethyl group, and 3,3,3-trifluoropropyl group. It is more preferable that $R^d$ and $R^e$ are bonded together to form a cyclopentyl group, cyclohexyl group, or cycloheptyl group.

The above process represented by reaction formulas [1] to [3] is described in detail, as follows. At first, as shown in reaction formula [1], a fluorine-containing carboxylate (i) having an active halogen atom at α-position is reacted with a carbonyl compound (ii) in the presence of Zn under an anhydrous condition (Reformatsky reaction), thereby obtaining a hydroxy carboxylate (iii). Then, as shown in reaction formula [2], the hydroxy carboxylate (iii) is reacted in solvent with a halogen compound (iv) having a polymerizable double bond in the presence of a base, thereby obtaining an unsaturated carboxylate (v). Then, as shown in reaction formula [3], the carboxylate (v) is hydrolyzed into an unsaturated carboxylic acid (vi) having a fluorine atom at α-position. At last, the obtained unsaturated carboxylic acid (vi) is reacted in solvent with a halogen compound (vii) in the presence of a base, thereby obtaining a fluorine-containing compound (viii). It is clear that formula (vi) corresponds to formula (1) if "W'—O—$CR^dR^e$" is interpreted as W.

The solvent used in the reaction of reaction formulas [1] or [2] is not particularly limited, as long as it is not active in the reaction. Its examples include aliphatic hydrocarbons such as pentane, hexane and heptane; aromatic hydrocarbons such as benzene, toluene and xylene; nitrites such as acetonitrile, propionitrile, phenylacetonitrile, isobutyronitrile, and benzonitrile; acid amides such as dimethylformamide, dimethylacetamide, methylformamide, formamide, and hexamethylphosphoric triamide, $C_1$-$C_4$ lower ethers such as tetrahydrofuran, 1,2-dimethoxyethane, 1,4-dioxane, diethyl ether, 1,2-epoxyethane, 1,4-dioxane, dibutyl ether, tert-butyl methyl ether, and substituted tetrahydrofurans. Of these dimethylformamide and tetrahydrofuran are preferable. These solvents can be used in combination. The amount of the solvent may be about 1-100 parts by weight, preferably 1-10 parts by weight, relative to one part by weight of the starting material.

It is preferable to remove water as much as possible from the solvent to be used in the reaction of reaction formula [1]. The water content of this solvent is more preferably 50 ppm or less.

It is also preferable to remove water as much as possible from the solvent to be used in the reaction of reaction formulas [2]. It is, however, not necessary to completely remove water from this solvent. Its water content close to that is generally contained in an industrially available solvent is not problematic in conducting the reaction. Therefore, such solvent can be used without removing water.

It is preferable to activate zinc by a known method for its use in the reaction of reaction formula [1]. Its exemplary methods include a method using metallic zinc obtained by reducing a zinc salt (e.g., zinc chloride) with potassium, magnesium, lithium or the like; a method for activating metallic zinc by treating metallic zinc with hydrochloric acid; a method for activating zinc by treating metallic zinc with a copper salt or silver salt in acetic acid to convert metallic zinc into an alloy of zinc and copper or silver; a method for activating zinc by ultrasonic waves; a method for activating zinc by mixing metallic zinc with chlorotrimethylsilane in ether; and a method for activating zinc by bringing metallic zinc into contact with chlooromethylsilane and a copper compound in an aprotic organic solvent.

Zinc may have any form, such as powder, granule, aggregate, porous form, cutting scrap, or filament. The reaction temperature for conducting the reaction of reaction formula [1] may be about −78 to 120° C. Its reaction time may be 10 minutes to 20 hours for convenience, although it varies depending on the reaction agents. Its reaction pressure may be around ordinary pressure. Its other reaction conditions may be the same as those of known analogous reactions using metallic zinc therein.

Examples of the base used in the reactions of reaction formula [2] include organic bases, such as trimethylamine, triethylamine, diisopropylethylamine, tri-n-propylamine, tri-n-butylamine, dimethyllaurylamine, dimethylaminopyridine, N,N-dimethylaniline, dimethylbenzylamine, 1,8-diazabicyclo[5,4,0]undec-7-ene, 1,4-diazabicyclo[2,2,2]octane, pyridine, 2,4,6-trimethylpyridine, pyrimidine, pyridazine, 3,5-lutidine, 2,6-lutidine, 2,4-lutidine, 2,5-lutidine, and 3,4-lutidine. Of these, triethylamine, diisopropylethylamine, dimethylaminopyridine, 1,8-diazabicyclo [5,4,0] undec-7-ene, pyridine, and 2,6-lutidine are preferable.

The amount of the base to be used in the reaction of reaction formula [2] may be 1 mol or greater, generally preferably 1-10 moles, particularly more preferably 1-5 moles, per mol of the substrate.

Similar to the reaction of reaction formula [1], the reaction temperature for conducting the reaction of reaction formula [2] may be about −78 to 120° C. Their reaction time may be 10 minutes to 20 hours for convenience, although it varies depending on the reaction agents. Their reaction pressure may be around ordinary pressure. Their other reaction conditions may be the same as those of known analogous reactions.

The reaction of reaction formula [3] is conducted by hydrolyzing the substrate (v) with water in the presence of a basic substance that may be the above-mentioned organic base or an inorganic basic substance (e.g., sodium hydroxide, potassium hydroxide, sodium carbonate, and calcium hydroxide).

It is possible to conduct a purification operation (e.g., washing, separation of solvent, etc., and drying) after each reaction of reaction formulas [1] to [3].

COMPONENT (B)

Acid Generator for Generating Acid by Exposure

The acid generator for generating acid by exposure is not particularly limited, and it is possible to use one of acid generators for chemically amplified resist, which have been proposed up to now. Examples of such acid generator include onium salt series acid generators (e.g., iodonium salts and sulfonium salts), oximesulfonate series acid generators, diazomethane series acid generators (e.g., bisalkyl or bisarylsulfonyl diazomethanes and poly(bissulfonyl)diazomethanes), nitrobenzylsulfonate series acid generators, iminosulfonate series acid generators, and disulfone series acid generators.

Examples of onium salt series acid generators include 1-phenyltetrahydrothiophenium trifluoromethanesulfonate or nonafluoro-n-butanesulfonate, 1-(4-hydroxyphenyl)tetrahydrothiophenium trifluoromethanesulfonate or nonafluoro-n-butanesulfonate, 1-(4-n-butoxynaphthalene-1-yl) tetrahydrothiophenium trifluoromethanesulfonate or nonafluoro-n-butanesulfonate, and 1-(3,5-dimethyl-4-hydroxyphenyl)tetrahydrothiophenium trifluoromethanesulfonate or nonafluoro-n-butanesulfonate.

Specific examples of onium salt series acid generators include diphenyliodonium trifluoromethanesulfonate or nonafluorobutanesulfonate, bis(4-tert-butylphenyl)iodonium trifluoromethanesulfonate or nonafluorobutanesulfonate, triphenylsulfonium trifluoromethanesulfonate, heptafluoropropanesulfonate or nonafluorobutanesulfonate, tri(4-methylphenyl)sulfonium trifluoromethanesulfonate, heptafluoropropanesulfonate or nonafluorobutanesulfonate, dimethyl(4-hydroxynaphthyl)sulfonium trifluoromethanesulfonate, heptafluoropropanesulfonate or nonafluorobutanesulfonate, monophenyldimethylsulfonium trifluoromethanesulfonate, heptafluoropropanesulfonate or nonafluorobutanesulfonate, diphenylmonomethylsulfonium trifluoromethanesulfonate, heptafluoropropanesulfonate or nonafluorobutanesulfonate, (4-methylphenyl)diphenylsulfonium trifluoromethanesulfonate, heptafluoropropanesulfonate or nonafluorobutanesulfonate, (4-methoxyphenyl) diphenylsulfonium trifluoromethanesulfonate, heptafluoropropanesulfonate or nonafluorobutanesulfonate, tri(4-tert-butyl)phenylsulfonium trifluoromethanesulfonate, heptafluoropropanesulfonate or nonafluorobutanesulfonate, and diphenyl(1-(4-methoxy)naphthyl)sulfonium trifluoromethanesulfonate, heptafluoropropanesulfonate or nonafluorobutanesulfonate. Furthermore, anion moiety of these onium salts may be replaced with methanesulfonate, n-propanesulfonate, n-butanesulfonate, or n-octanesulfonate.

Specific examples of oximesulfonate-series acid generators include α-(p-toluenesulfonyloxyimino)-benzylcyanide, α-(p-chlorobenzenesulfonyloxyimino)-benzylcyanide, α-(4-nitrobenzenesulfonyloxyimino)-benzylcyanide, α-(4- nitro-2-trifluoromethylbenzenesulfonyloxyimino)-benzyl-cyanide, α-(benzenesulfonyloxyimino)-4-chlorobenzylcyanide, α-(benzenesulfonyloxyimino)-2,4-dichlorobenzylcyanide, α-(benzenesulfonyloxyimino)-2,6-dichlorobenzylcyanide, α-(benzenesulfonyloxyimino)-4-methoxybenzylcyanide, α-(2-chlorobenzenesulfonyloxyimino)-4-methoxybenzylcyanide, α-(benzenesulfonyloxyimino)-thien-2-yl acetonitrile, α-(4-dodecylbenzenesulfonyloxyimino)-benzylcyanide, α-[(p-toluenesulfonyloxyimino)-4-methoxyphenyl]acetonitrile, α-[(dodecylbenzenesulfonyloxyimino)-4-methoxyphenyl]acetonitrile, α-(tosyloxyimino)-4-thienylcyanide, α-(methylsulfonyloxyimino)-1-cyclopentenyl acetonitrile, α-(methylsulfonyloxyimino)-1-cyclohexenyl acetonitrile, α-(methylsulfonyloxyimino)-1-cycloheptenyl acetonitrile, α-(methylsulfonyloxyimino)-1-cyclooctenyl acetonitrile, α-(trifluoromethylsulfonyloxyimino)-1-cyclopentenyl acetonitrile, α-(trifluoromethylsulfonyloxyimino)-1-cyclohexyl acetonitrile, α-(ethylsulfonyloxyimino)ethyl acetonitrile, α-(propylsulfonyloxyimino)propyl acetonitrile, α-(cyclohexylsulfonyloxyimino)cyclopentyl acetonitrile, α-(cyclohexylsulfonyloxyimino)cyclohexyl acetonitrile, α-(cyclohexylsulfonyloxyimino)-1-cyclopentenyl acetonitrile, α-(ethylsulfonyloxyimino)-1-cyclopentenyl acetonitrile, α-(isopropylsulfonyloxyimino)-1-cyclopentenyl acetonitrile, α-(n-butylsulfonyloxyimino)-1-cyclopentenyl acetonitrile, α-(ethylsulfonyloxyimino)-1-cyclohexenyl acetonitrile, α-(isopropylsulfonyloxyimino)-1-cyclohexenyl acetonitrile, α-(n-butylsulfonyloxyimino)-1-cyclohexenyl acetonitrile, α-(methylsulfonyloxyimino)phenyl acetonitrile, α-(methylsulfonyloxyimino)-p-methoxyphenyl acetonitrile, α-(trifluoromethylsulfonyloxyimino)phenyl acetonitrile, α-(trifluoromethylsulfonyloxyimino)-p-methoxyphenyl acetonitrile, α-(ethylsulfonyloxyimino)-p-methoxyphenyl acetonitrile, α-(propylsulfonyloxyimino)-p-methylphenyl acetonitrile, and α-(methylsulfonyloxyimino)-p-bromophenyl acetonitrile.

Of diazomethane series acid generators, specific examples of bisalkyl or bisarylsulfonyl diazomethane include bis(isopropylsulfonyl)diazomethane, bis(p-toluenesulfonyl)diazomethane, bis(1,1-dimethylethylsulfonyl)diazomethane, bis(cyclohexylsulfonyl)diazomethane, and bis(2,4-dimethylphenylsulfonyl)diazomethane.

Specific examples of poly(bissulfonyl)diazomethane include 1,3-bis(phenylsulfonyldiazomethylsulfonyl)propane, 1,4-bis(phenylsulfonyldiazomethylsulfonyl)butane, 1,6-bis(phenylsulfonyldiazomethylsulfonyl)hexane, 1,10-bis(phenylsulfonyldiazomethylsulfonyl)decane, 1,2-bis(cyclohexylsulfonyldiazomethylsulfonyl)ethane, 1,3-bis(cyclohexylsulfonyldiazomethylsulfonyl)propane, 1,6-bis(cyclohexylsulfonyldiazomethylsulfonyl)hexane, and 1,10-bis(cyclohexylsulfonyldiazomethylsulfonyl)decane.

These acid generators may be used singly or in combination of at least two kinds.

In particular, it is preferable to use an oxime sulfonate series acid generator, such as bis-o-(n-butylsulfonyl)-α-dimethyl glyoxime, in a lithography using electron beam. It is preferable to use an onium salt containing a fluorinated alkylsulfonic acid ion as its anionic moiety, such as triphenylsulfonium trifluoromethanesulfonate, in a lithography using ArF excimer laser.

The content of the acid generator in the negative-type resist composition of the present invention may be 0.5-30 parts by weight, preferably 1-10 parts by weight, relative to 100 parts by weight of the alkali-soluble resin component. If it is in the range of 0.5-30 parts by weight, the pattern formation is sufficiently conducted. Furthermore, it is possible to obtain a homogeneous solution as the negative-type resist composition. Thus, its storage stability is improved.

COMPONENT (C)

Crosslinking Agent

The crosslinking agent can be selected from conventional crosslinking agents used for chemically amplified negative-type resist compositions.

Specifically, it is possible to use compounds obtained by reacting an amino group-containing compound (e.g., melamine, acetoguanamine, benzoguanamine, urea, ethylene urea, propylene urea, glycol uril) with formaldehyde or with formaldehyde and lower alcohol to replace a hydrogen atom of the amino group with a hydroxymethyl or lower alkoxymethyl group. Of these compounds, those obtained by using melamine are referred to melamine series crosslinking agent. Those obtained by using urea are referred to as urea series crosslinking agent. Those obtained by using alkylene urea (e.g., ethylene urea and propylene urea) are referred to as alkylene urea series crosslinking agent. Those obtained by using glycol uril are referred to as glycol uril series crosslinking agent. The crosslinking agent is preferably at least one selected from melamine series crosslinking agent, urea series crosslinking agent, alkylene urea series crosslinking agent, and glycol uril series crosslinking agent. In particular, glycol uril series crosslinking agent is preferable.

Examples of melamine series crosslinking agent include hexamethoxymethylmelamine, hexaethoxymethylmelamine, hexapropoxymethylmelamine, and hexabutoxybutylmelamine. In particular, hexamethoxymethylmelamine is preferable.

Examples of urea series crosslinking agent include bismethoxymethyl urea, bisethoxymethyl urea, bispropoxymethyl urea, and bisbutoxymethyl urea. In particular, bismethoxymethyl urea is preferable.

Examples of alkylene urea series crosslinking agent include ethylene urea series crosslinking agents, such as mono and/or dihydroxymethylated ethylene urea, mono and/or dimethoxymethylated ethylene urea, mono and/or diethoxymethylated ethylene urea, mono and/or dipropoxymethylated ethylene urea, and mono and/or dibutoxymethylated ethylene urea, propylene urea series crosslinking agents, such as mono and/or dihydroxymethylated propylene urea, mono and/or dimethoxymethylated propylene urea, mono and/or diethoxymethylated propylene urea, mono and/or dipropoxymethylated propylene urea, and mono and/or dibutoxymethylated propylene urea, 1,3-di(methoxymethyl)-4,5-dihydroxy-2-imidazolidinone, and 1,3-di(methoxymethyl)-4,5-dimethoxy-2-imidazolidinone.

Examples of glycol uril series crosslinking agent include mono, di, tri and/or tetrahydroxymethylated glycol uril, mono, di, tri and/or tetramethoxymethylated glycol uril, mono, di, tri and/or tetraethoxymethylated glycol uril, mono, di, tri and/or tetrapropoxymethylated glycol uril, mono, di, tri and/or tetrabutoxymethylated glyocl uril.

The crosslinking agent may be used singly or in combination of at least two kinds. The content of the crosslinking agent in the negative-type resist composition of the present invention is preferably 3-30 parts by weight, more preferably 3-25 parts by weight, the most preferably 5-20 parts by weight, relative to 100 parts by weight of the alkali-soluble resin component. If it is 3 parts by weight or greater, the crosslink formation can proceed sufficiently to obtain a good resist pattern. If it is 30 parts by weight or less, the resist composition can have good storage stability, and it is possible to suppress sensitivity lowering over time.

COMPONENT (D)

Nitrogen-Containing Organic Compound

The negative-type resist composition of the present invention may contain a nitrogen-containing organic compound as an optional component (D) for improving resist pattern shape, its stability over time, etc.

This nitrogen-containing organic compound may be selected various conventional ones, for example, aliphatic amines, particularly preferably secondary aliphatic amines and tertiary aliphatic amines.

The aliphatic amine may be an alkyl amine or alkylalcohol amine, in which at least one hydrogen atom of ammonia $NH_3$ has been replaced with a $C_1$-$C_{12}$ alkyl or hydroxyalkyl group. Its specific examples include monoalkyl amines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine, and tri-n-dodecylamine; alkylalcohol amines such as diethanolamine, triethanolamine, diisopropanolamine, triisopropanolamine, di-n-octanolamine, and tri-n-octanolamine. Of these, alkylalcohol amines and trialkylamines are preferable, and alkylalcohol amines are the most preferable. Of alkylalcohol amines, triethanolamine and triisopropanolamine are the most preferable.

These amines may be used singly or in combination of at least two kinds.

The nitrogen-containing organic compound may generally be in 0.01-5.0 parts by weight relative to 100 parts by weight of the alkali-soluble resin component.

COMPONENT (E)

Organic Carboxylic Acid or Phosphorus Oxoacid or its Derivative

The negative-type resist composition of the present invention may further contain an organic carboxylic acid or phosphorus oxoacid or its derivative as an optional component (E) for preventing sensitivity lowering and improving resist pattern shape and its stability over time. It is optional to select one or both of components (D) and (E).

Preferable examples of the organic carboxylic acid include malonic acid, citric acid, malic acid, succinic acid, benzoic acid, and salicylic acid.

Examples of the phosphorus oxoacid or its derivative include phosphoric acid and its derivatives (e.g., di-n-butyl phosphate and diphenyl phosphate), phosphonic acid and its derivatives (e.g., dimethyl phosphonate, di-n-butyl phosphonate, phenyl phosphonate, and diphenyl phosphonate), and phosphinic acid and its derivatives (e.g., phenyl phosphinate). Of these, phosphonic acid is particularly preferable.

The component (E) may be in 0.01-5.0 parts by weight relative to 100 parts by weight of the alkali-soluble resin component.

According to need, the negative-type resist composition of the present invention may contain additives that are miscible with the resist composition, for example, various additives such as additional resins for improving properties of the resist film, surfactant for improving coatability, dissolution inhibitor, plasticizer, stabilizer, coloring agent, antihalation agent, and dye

Solvent

As a process for forming the fluorine-containing polymer compound according to the present invention into a thin film, it is possible to use a process having the steps of dissolving the fluorine-containing polymer compound in an organic solvent, applying the coating solution to a substrate, and drying the film. The organic solvent is not particularly limited, as long as the fluorine-containing polymer compound is soluble therein. Examples of the organic solvent include (a) lactones such as γ-butyrolactone; (b) ketones such as acetone, methyl ethyl ketone, cyclohexanone, methyl isoamyl ketone, and 2-heptanone; (c) polyhydric alcohols and their derivatives such as ethylene glycol, ethylene glycol monoacetate, diethylene glycol, diethylene glycol monoacetate, propylene glycol, propylene glycol monoacetate, dipropylene glycol, and monomethyl ether, monoethyl ether, monopropyl ether, monobutyl ether or monophenyl ether of dipropylene glycol monoacetate; (d) cyclic ethers such as dioxane; (e) esters such as methyl lactate, ethyl lactate, methyl acetate, ethyl acetate, butyl acetate, methyl pyruvate, ethyl pyruvate, methyl methoxypropionate, and ethyl ethoxypropionate; (f) aromatic solvents such as xylene and toluene; (g) fluorine-containing solvents such as chlorofluorocarbons, alternatives for chlorofluorocarbons, perfluoro compounds, and hexafluoroisopropyl alcohol; (h) terpene-series petroleum naphtha solvents (high-boiling-point weak solvents) for improving coatability; and (i) paraffin-series solvents.

Of these solvents, propylene glycol monomethyl ether acetate (PGMEA), propylene glycol monomethyl ether (PGME), and ethyl lactate (EL) are preferable, and PGME is more preferable.

The solvents may be used singly or in a mixture of at least two kinds. It is preferable to use a mixed solvent of PGMEA and a polar solvent. The weight ratio of PGMEA to a polar solvent may suitably be determined in view of their compatibility, etc. This ratio is preferably 1:9 to 9:1, more preferably 2:8 to 8:2. Specifically, in the case of using EL as the polar solvent, the ratio is preferably 1:9 to 9:1, more preferably 2:8 to 8:2. In the case of using PGME as the polar solvent, the ratio is preferably 1:9 to 9:1, more preferably 2:8 to 8:2, still more preferably 3:7 to 7:3.

Furthermore, it is preferable to use a mixed solvent of at least one of PGMEA and EL and γ-butyrolactone. In this case, the weight ratio of at least one of PGMEA and EL to γ-butyrolactone is preferably 70:30 to 95:5.

The amount of the solvent is not particularly limited, and it may suitably be determined according to the resist film thickness to have a concentration, making it possible to apply the resist composition on substrate, etc. In general, the amount of the solvent is adjusted such that solid matter concentration of the resist composition becomes 2-25 wt %, preferably 5-20 wt %.

Resist Pattern Forming Method

A resist pattern forming method of the present invention may be conducted, for example, as follows.

Firstly, the negative-type resist composition is applied on substrate, followed by conducting a prebaking under a temperature condition of 80 to 150° C. for 40 to 120 seconds, preferably 60 to 90 seconds. Then, the film is exposed, for example, to electron beam or ArF excimer laser light with an ArF exposure apparatus through a desired mask pattern. Then, the film is subjected to a post exposure baking (PEB) under a temperature condition of 80 to 150° C. for 40 to 120 seconds, preferably for 60 to 90 seconds. Then, the film is subjected to a development treatment using a developing solution, for example, an alkali aqueous solution such as 0.1-10 wt % tetramethylammonium hydroxide aqueous solution. This forming method makes it possible to obtain a pattern conforming to the mask pattern.

The substrate is, for example, a silicon wafer. It is also possible to use an inorganic substrate coated with a film of SiON, SiN or the like. It is optional to provide an organic or inorganic antireflective film between the substrate and the resist film.

Wavelength used for exposure is not particularly limited. In case that the fluorine-containing polymer compound contains no aromatic group in its structure, it is possible to conduct exposure by using a high-energy ray such as ArF excimer laser, KrF excimer laser, $F_2$ excimer laser, extreme ultraviolet ray (EUV), vacuum ultraviolet ray (VUV), electron beam (EB), X-ray, or soft X-ray.

The present invention makes it possible to form a resist pattern that is high in rectangularity. For example, it is possible to suppress a so-called film decrease phenomenon in which a top portion of the resist pattern becomes round by development.

In the following, the present invention is described in detail by examples, but it is not limited to these examples.

EXAMPLE 1

Synthesis of ethyl 2,2-difluoro-3-hydroxy pentanoate Represented by the Following Formula

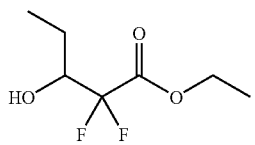

A 500 mL reactor was charged with 24.2 g (370 mmol, 1.3 eq) of activated metallic zinc and 300 mL of tetrahydrofuran (THF) (dehydrated one), followed by adding in a dropwise manner an ethyl bromo-difluoro acetate/THF solution prepared by adding 51.47 g (253.6 mmol, 1.0 eq) of ethyl bromo-difluoro acetate to 80 mL of THF (dehydrated one). After the dropping, stirring was conducted at room temperature for 20 minutes, followed by adding a propionaldehyde/THF solution prepared by adding 14.80 g (254.8 mmol, 1.0 eq) of propionaldehyde to 80 mL of THF (dehydrated one), and then stirring at room temperature fro 30 minutes. Then, water and diisopropyl ether were added, followed by separation of an organic layer from an aqueous layer. The obtained organic layer was washed with diluted hydrochloric acid and water, followed by removing water with magnesium sulfate, filtration, and distilling the diisopropyl ether off, thereby obtaining 41.2 g of the target ethyl 2,2-difluoro-3-hydroxy pentanoate. The yield was 89%.

The property of ethyl 2,2-difluoro-3-hydroxy pentanoate was as follows.

$^1$H NMR (CDCl$_3$) δ 4.31 (q, J=7.1 Hz, 2H; CH$_2$—O), 3.89 (m, 1H; CH—OH), 2.50 (br, 1H; OH), 1.71 (m, 1H), 1.52 (m, 1H), 1.32 (t, J=7.1 Hz, 3H; CH$_3$), 1.02 (t, J=7.3 Hz, 3H; CH$_3$)

$^{19}$F NMR (CDCl$_3$) d −115.26 (d, J=252 Hz, 1F), −122.95 (d, J=252 Hz, 1F)

EXAMPLE 2

Production of 1-ethoxycarbonyl-1,1-difluoro-2-butyl methacrylate Represented by the Following Formula

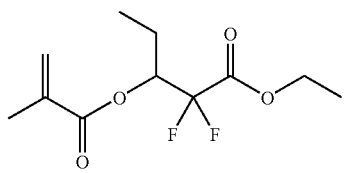

A 25 ml reactor was charged with 1.50 g (8.2 mmol) of ethyl 2,2-difluoro-3-hydroxypentanoate, 6.5 g of chloroform, 10 mg of an antioxidant NONFLEX MBP made by Seiko Chemical Co., Ltd., 1.03 g (9.9 mmol, 1.2 eq) of methacrylic chloride, and 1.25 g (12.4 mmol, 1.5 eq) of triethylamine, followed by stirring at 55° C. for 4 hours. Then, 10 g of water was added, followed by extraction with chloroform one time. The obtained organic layer was washed with diluted hydrochloric acid and water, followed by removing water with magnesium sulfate. After conducting filtration, chloroform was distilled off, thereby obtaining 2.06 g of the target 1-ethoxycarbonyl-1,1-difluoro-2-butyl methacrylate. Purity was 66%, and yield was 66%.

The property of 1-ethoxycarbonyl-1,1-difluoro-2-butyl methacrylate was as follows.

$^1$H NMR (CDCl$_3$) d 6.14 (s, 1H; methylene), 5.62 (s, 1H; methylene), 5.35 (m, 1H; CH—O), 4.27 (m, 2H; CH$_2$—O), 1.93 (s, 3H; CH$_3$), 1.81 (m, 2H; CH$_2$), 1.28 (t, J=7.2 Hz, 3H; CH$_3$), 0.95 (t, J=7.6 Hz, 3H; CH$_3$)

$^{19}$F NMR (CDCl$_3$) d −113.63 (d, J=264 Hz, 1F), −119.57 (d, J=264 Hz, 1F)

EXAMPLE 3

Production of 1-hydroxycarbonyl-1,1-difluoro-2-butyl methacrylate, methacrylic acid (1), Represented by the Following Formula

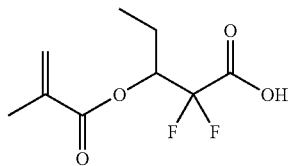

A 25 mL reactor was charged with 1.00 g (2.6 mmol) of 1-ethoxycarbonyl-1,1-difluoro-2-butyl methacrylate (purity: 66%) and 1.00 g of water, followed by cooling to 0° C., adding 1.06 g (4.0 mmol, 1.5 eq) of 15 wt % sodium hydroxide aqueous solution in a dropwise manner, and then stirring at room temperature for 1 hr. The reaction solution was washed with 10 g of diisopropyl ether. The obtained aqueous layer was washed with diluted hydrochloric acid, followed by extraction with diisopropyl ether two times, removal of water with magnesium sulfate, filtration, and then distilling diisopropyl ether off, thereby obtaining 0.19 g of the target methacrylic acid (1). Upon this, purity was 78%, and yield was 27%.

The property of methacrylic acid (1) was as follows.

$^{1}$H NMR (CDCl$_3$) d 7.24 (br, 1H; COOH), 6.16 (s, 1H; methylene), 5.63 (s, 1H; methylene), 5.39 (m, 1H; CH—O), 1.93 (s, 3H; CH$_3$), 1.85 (m, 2H; CH$_2$), 0.97 (t, J=7.6 Hz, 3H; CH$_3$)

$^{19}$F NMR (CDCl$_3$) d −114.24 (d, J=264 Hz, 1F), −119.48 (d, J=264 Hz, 1F)

EXAMPLE 4

Synthesis of fluorine-containing polymer compound (1), as Shown in the Following Formula

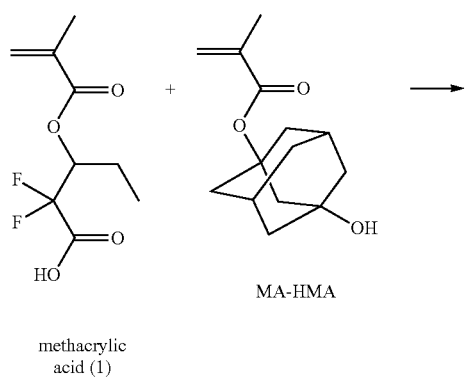

A 100 mL round-bottom flask equipped with a reflux condenser and a stirrer was charged with 1.80 g of methacrylic acid (1), 4.47 g of hydroxyadamantyl methacrylate (MA-HMA made by DAICEL CHEMICAL INDUSTRIES, LTD.), 0.11 g of azobisisobutyronitrile (AIBN), and 15.0 mL of methyl ethyl ketone, followed by replacing the inside of the flask with nitrogen. While the flask was heated in an oil bath at 60° C., stirring was conducted for 18 hr to conduct the reaction. After the reaction, 60 ml of n-hexane was added, followed by stirring. The resulting precipitate was taken out of the flask, followed by drying at 55° C. for 18 hr, thereby obtaining 4.57 g of fluorine-containing polymer compound (1) in a white solid. Yield was 73%. The compositional molar ratio (p/q) of fluorine-containing polymer compound (1) was determined by NMR. The molecular weight was determined by gel permeation chromatography (GPC; standard substance: polystyrene). The results are shown in Table 1.

EXAMPLE 5

Synthesis of fluorine-containing polymer compound (2), as Shown in the Following Formula

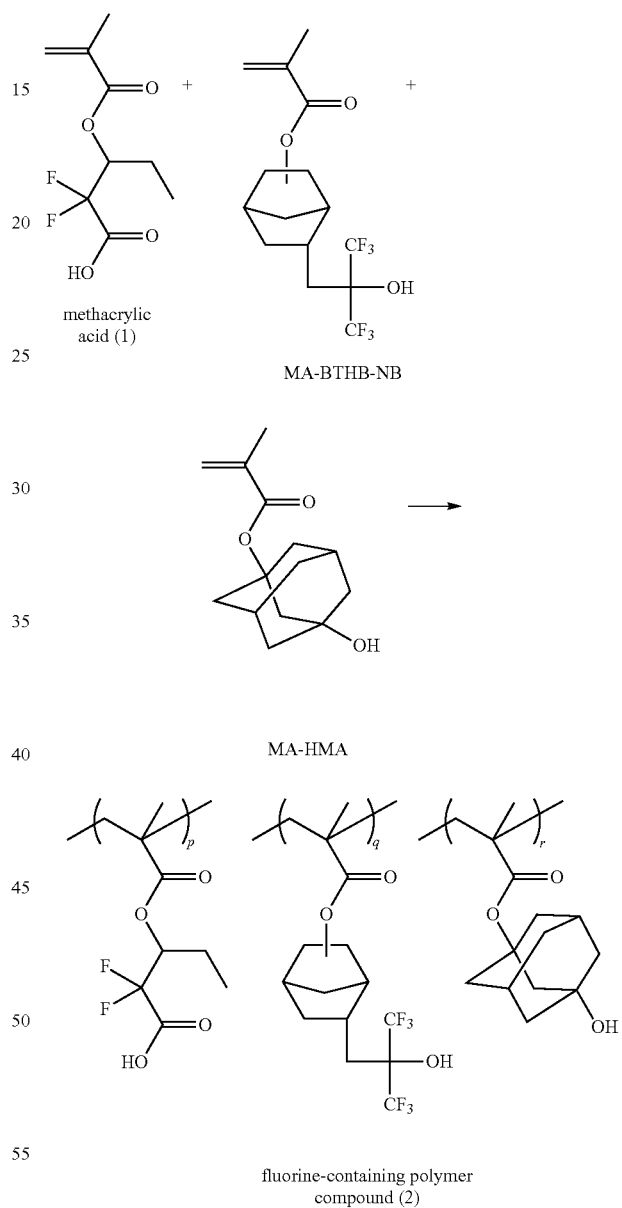

Similar to the process of Example 4, a copolymerization was conducted by using three raw materials, methacrylic acid (1), MA-BTHB-NB synthesized by the process according to Japanese Patent Application Publication 2004-175740, of which disclosure is incorporated herein by reference, and MA-HMA, thereby synthesizing fluorine-containing polymer compound (2) in a white solid. The results are shown in Table 1.

EXAMPLE 6

Synthesis of fluorine-containing polymer compound (3), as Shown in the Following Formula

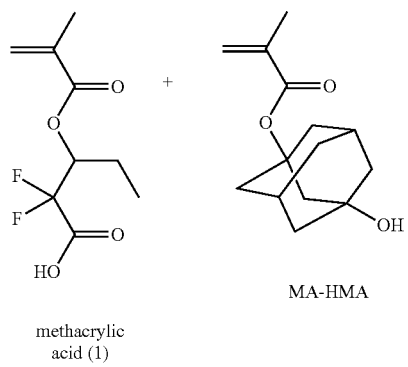

methacrylic acid (1)    MA-HMA

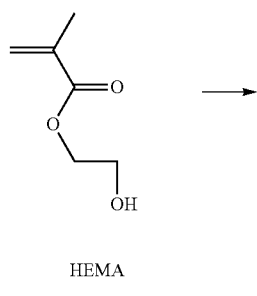

HEMA

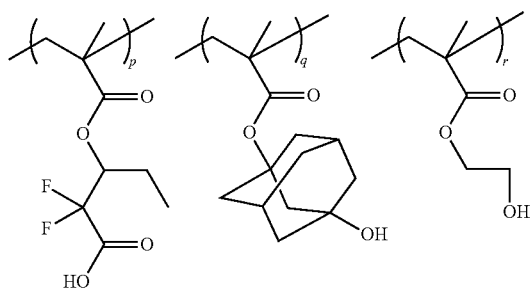

fluorine-containing polymer compound (3)

Similar to the process of Example 4, a copolymerization was conducted by using three raw materials, methacrylic acid (1), MA-HMA, and HEMA made by TOKYO CHEMICAL INDUSTRY CO., LTD., thereby synthesizing fluorine-containing polymer compound (3) in a white solid. The results are shown in Table 1.

COMPARATIVE EXAMPLE 1

Synthesis of fluorine-containing polymer compounds (4) and (5), as Shown in the Following Formula

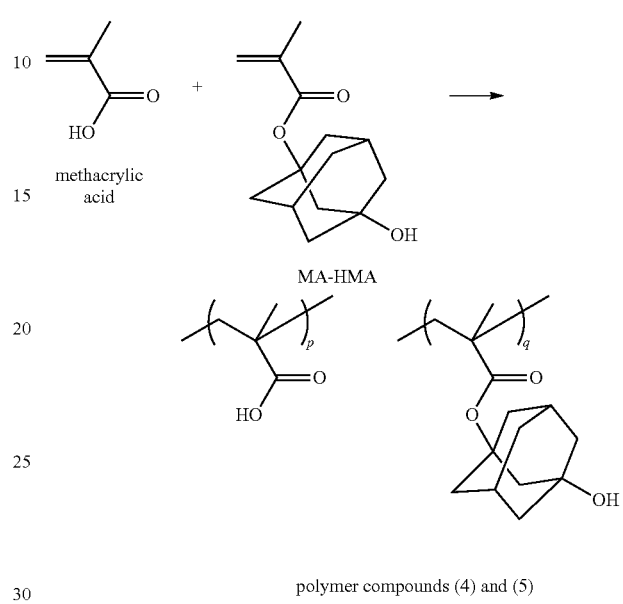

methacrylic acid    MA-HMA polymer compounds (4) and (5)

Similar to the process of Example 4, two copolymerizations were conducted by using two raw materials, methacrylic acid and MA-HMA, thereby synthesizing fluorine-containing polymer compounds (4) and (5) in white solids. The results are shown in Table 1.

TABLE 1

| | Polymer Compound No. | Molecular Weight Mw (Mw/Mn) | Compositional Molar Ratio | Solubility in Developing Solution |
|---|---|---|---|---|
| Ex. 4 | (1) | 17,100 (2.04) | 35/65 (p/q) | soluble |
| Ex. 5 | (2) | 15,100 (1.89) | 31/35/34 (p/q/r) | soluble |
| Ex. 6 | (3) | 14,800 (1.85) | 29/35/36 (p/q/r) | soluble |
| Com. Ex. 1 | (4) | 16,200 (1.94) | 29/71 (p/q) | insoluble |
| Com. Ex. 1 | (5) | 15,800 (2.14) | 37/63 (p/q) | soluble |

Solubility Test 0.5 g of polymer compounds (1) to (5) were each added to 10 cc of 2.38 wt % tetramethylammonium hydroxide aqueous solution, followed by maintaining it at 22° C. for 1 minute. When solid matter was recognized in it by observation with naked eyes, it was judged as insoluble in the developing solution. When solid matter was not recognized in it, it was judged as soluble. The results are shown in Table 1.

EXAMPLE 7

Fluorine-containing polymer compounds (1), (2), (3), and (5) were each dissolved in propylene glycol methyl acetate, and they were adjusted to have a solid matter content of 14%. Furthermore, 5 parts by weight of triphenylsulfonium triflate (TPS105) made by Midori Kagaku Co., Ltd. as an acid generator and 10 parts by weight of a glycoluril series crosslinking agent, NIKALAC MX-270 (trade name), made by SANWA CHEMICAL CO., LTD. were dissolved per 100 parts by weight of the polymer compound, thereby preparing resist compositions (R-1, R-2, R-3, and R-5).

Then, all of the resist compositions were filtered with a membrane filer of a pore diameter of 0.2 μm. Then, each composition was applied to a silicon wafer by spin coating to obtain a resist film of a film thickness of 300 nm. After conducting a preliminary baking at 120° C., an exposure to a 248 nm ultraviolet ray was conducted through a photomask of a 200 nm-size, 1:1 line-and-space (200 nm 1L/1S pattern). Then, a post exposure baking was conducted at 120° C. Then, a development was conducted at 22° C. for 1 minute using 2.38 wt % tetramethylammonium hydroxide aqueous solution. As a result, a high-resolution pattern was obtained from each resist composition. There were not found inferiority defect in adhesion to substrate, film-forming inferiority defect, development defect, and etching resistance inferiority defect.

The 200 nm 1L/1S pattern was observed by a critical dimension scanning electron microscope (CD-SEM), S9220 (tradename) of Hitachi High-Technologies Corporation.

TABLE 2

| Resist Composition | Polymer Compound | Pattern Characteristic |
|---|---|---|
| R-1 | Fluorine-containing Polymer Compound (1) | Rectangular |
| R-2 | Fluorine-containing Polymer Compound (2) | Rectangular |
| R-3 | Fluorine-containing Polymer Compound (3) | Rectangular |
| R-5 | Polymer Compound (5) | Swelled |

As is clear from Table 2, the resist compositions R-1 to R-3 according to the present invention provided good results (i.e., rectangular patterns with no swelling, as compared with that R-5 of Comparative Example 1.

What is claimed is:

1. A fluorine-containing polymer compound comprising a repeating unit (a) obtained by cleavage of a polymerizable double-bond of a compound selected from the group consisting of the following compounds,

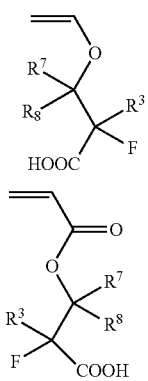
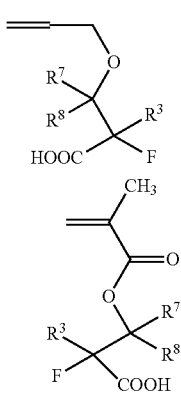
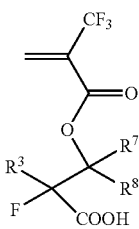
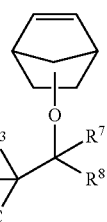
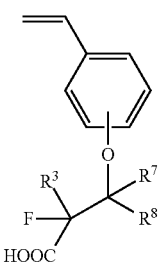

wherein $R^3$ represents a fluorine atom or trifluoromethyl group, $R^7$ represents a hydrogen atom or a straight-chain, branched or cyclic alkyl or fluoroalkyl group, $R^8$ represents a straight-chain, branched or cyclic alkyl or fluoroalkyl group, and $R^7$ and $R^8$ may be combined to form a ring, wherein the fluorine-containing polymer compound has a weight-average molecular weight of 1,000 to 1,000,000.

2. A fluorine-containing polymer compound according to claim 1, wherein each of $R^7$ and $R^8$ independently represents a $C_1$-$C_4$ straight-chain or branched alkyl or fluoroalkyl group or a $C_3$-$C_{10}$ cyclic alkyl or fluoroalkyl group, or $R^7$ and $R^8$ are bonded together to form a $C_4$-$C_8$ alicyclic hydrocarbon group.

3. A fluorine-containing polymer compound according to claim 1, wherein $R^7$ represents a hydrogen atom or a monovalent organic group selected from the group consisting of methyl group, ethyl group, propyl group, butyl group, cyclopentyl group, cyclohexyl group, norbornyl group, adamantyl group, trifluoromethyl group, 2,2,2-trifluoroethyl group, 1-(trifluoromethyl)ethyl group, and 3,3,3-trifluoropropyl group, $R^8$ represents a monovalent organic group selected from the group consisting of methyl group, ethyl group, propyl group, butyl group, cyclopentyl group, cyclohexyl group, norbornyl group, adamantyl group, trifluoromethyl group, 2,2,2-trifluoroethyl group, 1-(trifluoromethyl)ethyl group, and 3,3,3-trifluoropropyl group, or $R^7$ and $R^8$ are bonded together to form a cyclopentyl group, cyclohexyl group or cycloheptyl group.

4. A fluorine-containing polymer compound according to claim 1, wherein $R^3$ represents a fluorine atom.

5. A fluorine-containing polymer compound according to claim 1, which has a structure obtained by cleavage of a polymerizable double-bond of a fluorine-containing unsaturated carboxylic acid represented by one of the following formulas,

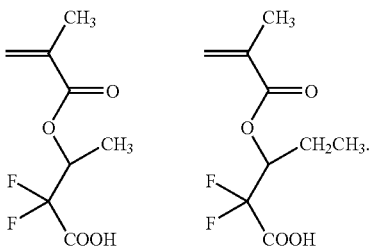

6. A fluorine-containing polymer compound according to claim 1, further comprising a repeating unit (b) having an alcoholic hydroxy group.

7. A fluorine-containing polymer compound according to claim 6, wherein the repeating unit (b) is a repeating unit represented by formula (7),

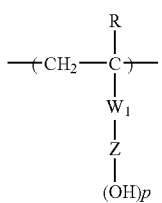
(7)

wherein R represents a hydrogen atom, alkyl group, halogenated alkyl group, halogen atom, or hydroxyalkyl group;
W1 represents a single bond, —C(=O)—O—, or —O—;
Z represents an alicyclic hydrocarbon group, an aliphatic acyclic hydrocarbon group, or an organic group formed of a combination of these groups, each of these groups having a valence of "p+1";
p represents an integer of 0-3; and
R represents a hydroxyalkyl group when p=0.

8. A fluorine-containing polymer compound according to claim 6, wherein the repeating unit (b) is a repeating unit represented by formula (7-1),

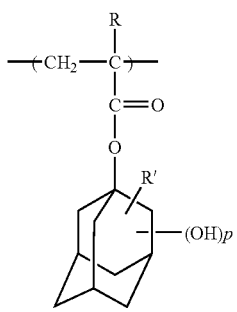
(7-1)

wherein R represents a hydrogen atom, alkyl group, halogen atom, or halogenated alkyl group;
R' represents a hydrogen atom, alkyl group, or $C_{1-5}$ alkoxy group; and
p represents an integer of 1-3.

9. A fluorine-containing polymer compound according to claim 6, further comprising a repeating unit (c) having a side chain with a lactone ring.

10. A fluorine-containing polymer compound according to claim 6, wherein the repeating unit (a) and the repeating unit (b) are respectively in 1-99 mol % and 1-90 mol %, based on a total mole number of all repeating units contained in the fluorine-containing polymer compound.

11. A fluorine-containing polymer compound according to claim 1, further comprising at least one repeating unit formed by cleavage of at least one polymerizable double bond of at least one compound selected from the group consisting of acrylates, fluorine-containing acrylates, methacrylates, fluorine-containing methacrylates, styrene compounds, fluorine-containing styrene compounds, vinyl ethers, fluorine-containing vinyl ethers, allyl ethers, fluorine-containing allyl ethers, acrylamides, methacrylamides, vinyl esters, allyl esters, olefins, fluorine-containing olefins, norbornene compounds, fluorine-containing norbornene compounds, sulfur dioxide, and vinyl silanes.

12. A fluorine-containing polymer compound according to claim 1, wherein the repeating unit (a) is in 1-99 mol %, based on a total mole number of all repeating units contained in the fluorine-containing polymer compound.

13. A fluorine-containing polymer compound according to claim 1, further comprising a repeating unit (b) having an alcoholic hydroxy group; a repeating unit (c) having a side chain with a lactone ring; and a repeating unit (d),
wherein the repeating unit (a) to (d) are respectively in 1-99 mol %, 1-90 mol %, 10-90 mol % and 0-70 mol %, based on a total mole number of all repeating units contained in the fluorine-containing polymer compound.

14. A negative-type resist composition comprising:
a fluorine-containing polymer compound according to claim 1, as an alkali-soluble resin component;
an acid generator for generating an acid by exposure; and
a crosslinking agent.

15. A process of using the negative-type resist composition according to claim 14 in the manufacture of a resist pattern, comprising the steps of:
(a) applying the negative-type resist composition according to claim 14 on a substrate to form a resist film;
(b) exposing the resist film; and
(c) developing the exposed resist film.

16. A process according to claim 15, wherein the step (b) is conducted by exposing the resist film to a high energy ray that is a near-ultraviolet ray, vacuum ultraviolet ray, extreme ultraviolet ray, or soft X-ray.

* * * * *